(12) United States Patent
Pfister et al.

(10) Patent No.: US 12,412,656 B2
(45) Date of Patent: Sep. 9, 2025

(54) METHOD FOR PROVIDING A CONTROL SIGNAL FOR CARRYING OUT A CURRENT OR NEXT WORKING STEP

(71) Applicant: Siemens Healthcare GmbH, Erlangen (DE)

(72) Inventors: Marcus Pfister, Bubenreuth (DE); Katharina Breininger, Erlangen (DE)

(73) Assignee: SIEMENS HEALTHINEERS AG, Forchheim (DE)

( * ) Notice: Subject to any disclaimer, the term of this patent is extended or adjusted under 35 U.S.C. 154(b) by 483 days.

(21) Appl. No.: 18/057,868

(22) Filed: Nov. 22, 2022

(65) Prior Publication Data

US 2023/0161602 A1    May 25, 2023

(30) Foreign Application Priority Data

Nov. 25, 2021   (DE) ...................... 10 2021 213 281.2

(51) Int. Cl.
| | |
|---|---|
| *G16H 40/40* | (2018.01) |
| *A61B 18/00* | (2006.01) |
| *A61B 90/00* | (2016.01) |
| *A61B 34/00* | (2016.01) |

(52) U.S. Cl.
CPC ............ *G16H 40/40* (2018.01); *A61B 18/00* (2013.01); *A61B 90/37* (2016.02); *A61B 34/25* (2016.02)

(58) Field of Classification Search
CPC ........ G16H 40/40; G16H 70/20; A61B 18/00; A61B 90/37
See application file for complete search history.

(56) References Cited

U.S. PATENT DOCUMENTS

| | | | | |
|---|---|---|---|---|
| 11,126,696 | B1* | 9/2021 | Srivastava | G16H 40/20 |
| 2014/0149129 | A1* | 5/2014 | Getchius | G06Q 40/08 |
| | | | | 705/2 |
| 2019/0006041 | A1* | 1/2019 | Chiofolo | G16H 50/20 |
| 2020/0335208 | A1* | 10/2020 | Talmor | G16H 40/60 |
| 2020/0365257 | A1* | 11/2020 | Xu | G16H 50/20 |
| 2022/0165418 | A1* | 5/2022 | Li | G06T 7/0012 |

OTHER PUBLICATIONS

Arbogast, N. et.al: "Workflow Phase Detection in Fluoroscopic Images Using Convolutional Neural Networks", in; Bildverarbeitung für die Medizin 2019.
Padoy N. et al.:"Machine and deep learning for workflow recognition during surgery" Minimally Invasive Therapy & Allied Technologies, 2019.
Behnke, S; Pfister, M.; Rojas, R.: , "A Study on the Combination of Classifiers for Handwritten Digit Recognition", in: Proceedings NN'98.

* cited by examiner

*Primary Examiner* — Jeong S Park
(74) *Attorney, Agent, or Firm* — Harness, Dickey & Pierce, P.L.C.

(57) ABSTRACT

A computer-implemented method comprises: provisioning a plurality of data streams, each of the plurality of data streams being assigned an individual classifier; provisioning a list including a plurality of possible working steps; applying the plurality of individual classifiers to the plurality of data streams, wherein for each working step, based on the assigned data stream, a probability is determined; determining a current or next working step as a function of the probabilities; and provisioning the control signal.

25 Claims, 11 Drawing Sheets

METHOD FOR PROVIDING A CONTROL SIGNAL FOR CARRYING OUT A CURRENT OR NEXT WORKING STEP

CROSS-REFERENCE TO RELATED APPLICATION(S)

The present application claims priority under 35 U.S.C. § 119 to German Patent Application No. 10 2021 213 281.2, filed Nov. 25, 2021, the entire contents of which are incorporated herein by reference.

FIELD

One or more example embodiments of the present invention relate to a computer-implemented method for providing a control signal for carrying out a current or next working step. One or more example embodiments of the present invention further relate to a system that is embodied for carrying out the method, to a computer program product and/or to a computer-readable memory medium.

BACKGROUND

The ever-advancing further development of technologies means that processes are becoming ever more complex. A complex process of this type can be a medical intervention on an examination object for example. The process is supported and/or carried out and/or monitored by one or more systems in such cases. The individual systems can provide information about a state of the examination object, a success or progress of the process etc. For example x-ray images of the examination object can be acquired during the process via a C-arm system by what is known as fluoroscopy. What is more the entire process can be monitored with an optical camera. It this way it can be shown for example in an overview image what members of the operating personnel who are carrying out the process, for example an operation team, are doing at a particular time. Further systems in a process can for example be a monitoring system for monitoring vital functions of the examination object and/or an endoscope and/or a robotic system for carrying out the intervention etc. The images, information etc. provided by a system will be referred to below in each case as the data stream.

The process typically comprises a plurality of working steps, which must be carried out in a specific sequence only variable under some conditions. Because of the complexity and the multilayered nature of the processes it is frequently difficult for the operating personnel or the operation team to keep an eye on the process as a whole. What is more it would be helpful if the systems that support the process were to automatically carry out the right working step at the right time. For example it would be helpful for carrying out the process if the C-arm system were to recognize when a new x-ray image is needed and from what angle relative to the examination object this x-ray image should be acquired. What is more a system supporting a process can for example indicate when it has completed its working step and the operation team can continue with a following working step. Many further applications in the medical environment and also in another environment are conceivable.

N. Padoy et al., "Machine and deep learning for workflow recognition during surgery.", Minimally Invasive Surgery and Allied Techniques, 2019, disclose a method that, based on a data stream of an individual system, can recognize which working step of a process is currently being carried out and is trained to predict the next working step. In this case a specific data stream, for example from an endoscope camera, is evaluated and the corresponding information is provided.

N. Arbogast et al., "Workflow Phase Detection in Fluoroscopic Images Using Convolutional Neural Networks", Bildverarbeitung für die Medizin (Image Processing for Medicine), 2019 describes a system for recognizing sections of the process and for determining a suitable collimation during acquisition of an x-ray image as a function of the section of the process.

S. Behnke, M. Pfister, R. Rojas, "A Study on the Combination of Classifiers for Handwritten Digit Recognition", In Proceedings of Neural Networks in Applications, Third International Workshop (NN'98), 1998 describe a method for combining different classifiers for recognition of handwritten digits.

It is known however that in a process, in particular a medical process, the data streams provided or the systems used vary. In this case the data streams provided can vary between different sections of the process. As an alternative or in addition different data streams can be provided in different institutions in which the same process is carried out. As an alternative or in addition different data streams can be provided as a function of a country in which the process is carried out. As an alternative or in addition the data streams provided can depend on the operation team carrying out the process.

With complex processes it is thus not possible to monitor and to control the process as a whole in each situation with the same data stream.

SUMMARY

An object of one or more example embodiments of the present invention is therefore to provide a method that makes it possible to control a process based on a plurality of data streams provided variably.

At least this object is achieved by a method for provision of a control signal for carrying out a current or next working step, by a system for provision of a control signal for carrying out a current or next working step, by a computer program product and by a computer-readable memory medium in accordance with one or more example embodiments of the present invention and/or the independent claims.

A way in which the inventive object is achieved is described below both with regard to the claimed apparatuses and also with regard to the claimed method. Features, advantages or alternate forms of embodiment mentioned here are likewise to be transferred to the other claimed subject matter and vice versa. In other words the physical claims (which are directed to an apparatus for example) can also be further developed with the features that are described or claimed in conjunction with a method. The corresponding functional features of the method are embodied in this case by corresponding physical modules.

Furthermore an inventive way in which the object is achieved is described both with regard to methods and apparatuses for provision of a control signal for carrying out a current or next working step and also with regard to methods and apparatuses for provision of individual classifiers or a trained function. In this context, features and alternate forms of embodiment of data structures and/or functions for methods and apparatuses for determination can be transferred to similar data structures and/or functions for methods and apparatuses for adaptation/optimization/training. Similar data structures here can in particular be characterized by being preceded by the word "training". Furthermore the individual classifiers used in methods and apparatuses for provision of the control signal for carrying out the current or next working step can in particular have been trained or adjusted and/or have been provided by methods for provision of the individual classifier.

One or more example embodiments of the present invention relate to a computer-implemented method for provision of a control signal for carrying out a current or next working step in a process. The method comprises a method step of provision of a plurality of data streams. In this case the process is divided into a plurality of consecutive process sections. In this case the data streams provided depend on a current process section. In this case each of the data streams is uniquely assigned an individual classifier. What is more the method comprises a method step of provision of a list comprising a plurality of possible working steps. What is more the method comprises a method step of application of individual classifiers to the respective assigned data stream, wherein each individual classifier, based on the data stream assigned, determines a probability for each working step that specifies how probable it is that the corresponding working step will be carried out as the next step. What is more the method comprises a method step of determining the current or next working step as a function of the probabilities determined. What is more the method comprises a method step of provision of the control signal for carrying out the current or next working step.

The process can in particular be a medical process. For example the process can be a medical intervention on an examination object, in particular into a human being or an animal. In other words the process can be carrying out a medical intervention. The medical intervention is in particular an operation. The process can then be carried out by an operation team. The operation team can comprise one or more medical specialists. The operation team can for example comprise an anesthetist, a surgeon and/or an operation assistant. etc.

The process is divided into the plurality of process sections. In other words the process comprises the plurality of process sections. The process sections must be carried out in a fixed order. The process sections can divide the process thematically into sections. When the process is a medical process the process sections can for example be an introduction of an anesthetic, an opening up of the examination object, a carrying out of an operation in the examination object, a sewing up of the examination object and a recovery from the anesthetic.

Each process section in this case comprises one or more working steps. A working step can be carried out manually in this case for example by one of the operating personnel carrying out the process, for example a member of an operation team, or automatically by a system. When the working step is an opening up of the examination object for example, the working step can be carried out manually by the surgeon of the operation team. When the working step is an acquisition of an x-ray image for example, the working step can be carried out by an x-ray system, for example a C-arm system.

The current working step specifies which working step is currently being carried out. The next working step specifies which working step is to be carried out after the current working step has begun, or after the current working step has been completed or ended.

In the method step of provision of the plurality of data streams, the data streams in particular can be received. In particular each data stream is provided by a system. The system in this case can in particular be a medical system. The data streams can thus be provided by a plurality of systems. In this case each data stream is suitable for or is embodied for describing the course of the process. In other words each of the data streams is embodied to describe at least one part, in particular at least one process. In other words each data stream can be suitable for describing one aspect of the process or at least one process section. Thus the expression "describe a process" means that at least one aspect of at least one section or part of the process is described by the data stream. For example a monitoring system that is embodied to monitor vital functions of the examination object can describe a progress of the vital functions during at least one process section. In this case the vital functions describe an aspect of the process. The data stream then comprises the data for the vital functions. Another aspect can for example be an overview of the process, which is recorded and provided by an optical camera. The corresponding data stream then comprises the image data provided by the optical camera. As an alternative a data stream can for example be at least one x-ray image or a voice command of the operating personnel etc.

Which data streams are provided depends on the current process section of the process. In other words the data streams can vary between different process sections. In particular the combination of data streams can vary between the process sections. A data stream can be provided in this case in precisely one process section or in more than one process section or in all process sections.

In this case an individual data stream of the plurality of data streams can also only be provided during a short period of time of the current process section. In other words a data stream does not have to be provided uninterrupted during the current process section.

Each of the data streams is assigned an individual classifier. The individual classifier is embodied to analyze the assigned data stream and, based on the data stream, to determine a probability as to which working step is currently being carried out and/or which working step should be the next to be carried out. In this case the individual classifier can be trained based on a default process as described below for example.

Data streams to which no individual classifier is assigned are not considered in this method. Despite this, such data streams can of course also be provided or received.

The individual classifiers are trained in advance on training data streams or training data to recognize and to extrapolate patterns. In this case the individual classifiers are trained individually or independently of one another. During the training at least one parameter of the individual classifier to be trained can be adapted.

In particular a supervised training, a semi-supervised training, an unsupervised training, a reinforcement learning and/or an active learning can be used. Over and above this representation learning (an alternative term is feature learning) can be used. In particular the at least one parameter of an individual classifier can be adapted iteratively by a number of training steps.

In particular an individual classifier can comprise a neural network, a support vector machine, a random tree or a decision tree and/or a Bayesian network, and/or an individual classifier can be based on k-means clustering, Q learning, genetic algorithms and/or association rules. In particular an individual classifier can comprise a combination of a number of uncorrelated decision trees or an ensemble consisting of decision trees (random forest). In particular an individual classifier can be determined via XGBoosting (eXtreme Gradient Boosting). In particular a neural network can be a deep neural network, a convolutional neural network or a convolutional deep neural network. Over and above this a neural network can be an adversarial network, a deep adversarial network and/or a generative adversarial network. In particular a neural network can be a recurrent neural network. In particular a recurrent neural network can be a network with long short-term memory (LSTM), in particular a gated recurrent unit (GRU). In particular an individual classifier can comprise a combination of the approaches described. In particular the approaches described here for an individual classifier are called the trained function network architecture.

A list comprising a plurality of possible working steps is provided in the method step of provision of the list. In particular the list is received in the method step.

The working steps comprised by the list can be process-specific in this case. In other words the list can comprise all possible working steps that are typically carried out at some point during the process.

As an alternative the working steps comprised by the list can be process section-specific. A separate specific list is then provided for each process section.

As an alternative the list can comprise all possible working steps that can be carried out during any given medical process. In this case the list is not restricted to those working steps that come into question for the current medical process. For example the list can then also comprise a working step of "connecting a heart-lung machine" when the process is an appendix operation.

In the method step of application of the individual classifiers each individual classifier is applied to the data stream assigned to it. In other words the correspondingly assigned individual classifier is applied to each of the provided data streams. For each data stream it is determined by the application of the correspondingly assigned individual classifier for each working step of the list how probable it is that the working step will be carried out as the current or as the next step. If no probability can be determined for a working step of the list for a data stream, the corresponding working step is assigned a probability of 0% or is assigned an NaN value or a default value. This working step is then handled in the same way as if the probability 0% had been determined for it.

In versions of example embodiments of the present invention, two probabilities can be determined for each working step. One of the probabilities can then specify the probability with which the corresponding working step is to be carried out currently and the other probability can specify the probability with which the corresponding working step is to be carried out as the next step.

In the method step of determination of the current or next working step, the current or the next working step is determined as a function of the previously determined probabilities. The "or" in this case is to be understood as a non-exclusive "or". In versions of example embodiments of the present invention, the current and the next working step can be determined. To determine the current and/or next working step the probabilities determined in the method step of application of the individual classifiers are analyzed and that working step or those working steps is or are determined that have the greatest probability of being carried out as the current or the next step. In this case the probabilities determined by the different individual classifiers can be analyzed as a function of the underlying data streams. For example the probabilities determined by an individual classifier assigned to a data stream determined can be weighted more heavily or more highly than the probabilities that are determined by an individual classifier assigned to another data stream. In this case the weightings of the individual classifiers can vary between the different process sections. For example a data stream that comprises information about a spoken command of a member of the operation teams is always weighted higher than a data stream of an overview camera. In this case the designation "weighting of the data stream" is synonymous with the designation "weighting of the probability that was determined by application of the assigned individual classifier to the data stream".

The control signal for carrying out the current or the next working step is provided in the method step of provision of the control signal. In this case the control signal that is to carry out the current or the next working step is in particular provided to the system. In this case the system that is to carry out the current or the next working step can be different from the systems that provide the data streams. As an alternative the system that is to carry out the current or the next working step can be comprised by the systems that provide the data streams. The control signal is embodied to control the system during carrying out of the current or next working step. The control signal is alternatively at least embodied to initiate the current or next working step at the system.

As an alternative or in addition the control signal can also be embodied to be provided to the operating personnel. For example the control signal can be embodied to be indicated. For example the working step that is being or is to be carried out as the current or next step can be indicated to the operating personnel on a screen. In this case the corresponding working step can be indicated on a screen for example in the form of a cue or a pictogram. As an alternative or in addition the control signal can be provided to the operating personnel in the form of an acoustic signal. For example a beep can announce a new working step. As an alternative the current or next working step can be announced in the form of a speech output.

The inventors have recognized that independent individual classifiers can be provided for the different data streams. In this way the individual classifiers for which the associated data streams are also actually provided can be applied flexibly. In this way the method can be adapted flexibly to different institutions or countries.

According to one aspect of an embodiment of the present invention, one of the provided data streams is an overview data stream. In this case the overview data stream is provided during the overall process. In this case overview data stream is in particular provided by a camera filming the process or via fluoroscopy. What is more the method in this case comprises a method step of determining the process section as a function of the overview data stream.

The overview data stream is comprised of the plurality of data streams provided. In this case the overview data stream is provided during the overall process. The other data streams provided can vary or differ between the individual process sections as described above. The overview data stream thus maps a course of the overall process. The overview data stream can be provided uninterrupted or continuously during the overall process. As an alternative the overview data stream can be provided in periods of time determined during the process provided. For example the overview data stream can be provided in each case at the beginning and/or at the end of a process section.

The overview data stream can in particular be provided by a camera filming the process. In this case the camera can for example be arranged on a ceiling of an operating theatre in which the process is being carried out or executed and film the process from a bird's-eye perspective. As an alternative the camera can be a combination of different cameras that film the process from different perspectives.

As an alternative the overview data stream can be provided via fluoroscopy. In the fluoroscopy x-ray images are acquired at specific intervals via a C-arm system. In other words in the fluoroscopy a time resolved "x-ray film" is acquired and provided. When the overview data stream is provided via fluoroscopy, the introduction of and recovery from the anesthetic is in particular not part of the process. Typically no x-ray images are acquired during the introduction of and recovery from the anesthetic and thus these steps are then not covered or comprised by the overview data stream.

In the method step of determination of the process section the process section is determined as a function of the overview data stream. In this case the process section in which the process currently finds itself is analyzed and determined in the overview data stream. For this for example a trained function can be applied to the overview data stream.

In general a trained function emulates cognitive functions that connect humans to human thought. In particular the trained function can be adapted to new circumstances and recognize and extrapolate functions through training based on training data.

In general parameters of a trained function can be adapted by training. In particular a supervised training, a semi-supervised training, an unsupervised training, a reinforcement learning and/or an active learning can be used for this. Over and above this representation learning (an alternative term is feature learning) can be used. In particular the parameters of the trained functions can be adapted iteratively by a number of training steps.

In particular a trained function can comprise a neural network, a support vector machine, a random tree or a decision tree and/or a Bayesian network, and/or the trained function can be based on k-means clustering, Q learning, genetic algorithms and/or association rules. In particular a trained function can comprise a combination of a number of uncorrelated decision trees or an ensemble of decision trees (random forest). In particular the trained function can be determined via XGBoosting (eXtreme Gradient Boosting). In particular a neural network can be a deep neural network, a convolutional neural network or a convolutional deep neural network). Over and above a neural network can be an adversarial network, a deep adversarial network and/or a generative adversarial network). In particular a neural network can be a recurrent neural network. In particular a recurrent neural network can be a network with long short-term memory, LSTM), in particular a gated recurrent unit (GRU). In particular a trained function can comprise a combination of the approaches described. In particular the approaches described here for a trained function are called the network architecture of the trained function.

For example, based on a behavior of the members of the operation team, it can be deduced in a data stream provided by a camera which process section is currently being carried out. As an alternative the current stage or process section of the process can be determined based on the x-ray images of the fluoroscopy. For example, based on the x-ray images, it can be determined whether a stent is already correctly positioned and whether a dilation of the stent should have been skipped for the process section.

In alternate versions of embodiments of the present invention, the overview data stream can also be different for each process section.

The inventors have recognized that the process section can be determined based on the overview data stream. In this way, with the help of the overview data stream, the process can be roughly divided into process sections. The inventors have recognized that it is typically known for different process sections what has to be carried out within the process section. In this way the determination of the current or next working step can be optimized in such a way that it is known that only one working step, which is actually carried out in the current process section, can also be the current or next working step. The inventors have recognized that in this way the method step of determination of the current or next working step can be simplified.

According to an optional aspect of an embodiment of the present invention, the list of working steps provided is adapted to the process section determined. In this case, in the method step of application of the individual classifiers to the respectively assigned data stream for each working step of the adapted list, a probability is determined that the corresponding working step will be the current or next step carried out.

The adaptation of the list of working steps provided is based in this case on the process section determined. In the adaptation of the list of working steps provided in particular only those working steps are retained in the list that might possibly be carried out in the process section determined. All working steps that will under no circumstances be carried out in the determined process section are deleted or removed from the adapted list. For this there can already be an assignment beforehand of working steps from the list to process sections.

For example in a process section "sewing up of the examination object" the working step "removal of the appendix" can have been removed from the adapted list of working steps.

The inventors have recognized that in this way computing power needed during application of the individual classifiers can be reduced. The inventors have recognized that probabilities that are already known in advance to be unlikely, since the corresponding working step is never or almost never carried out in the current process section, do not have to be computed. The inventors have recognized that this leads to a reduction in possible errors, since working steps not carried out in the process section also do not have to be considered. In other words working steps that are never or almost never carried out in the current process section are not available for determining the next or current working step and can thus also not be incorrectly determined as such.

According to a further aspect of an embodiment of the present invention, it is known which data streams will be determined in a process section provided. What is more in this case the method comprises a method step of provision of error information, which specifies that the process section determined is incorrect when a data stream is provided that is not expected in the process section determined.

It is thus known which data streams can be provided in the process section determined. In this case it does not conflict with the process section determined when fewer data streams are provided.

When a data stream is provided that is not expected for the process section determined, the error information is provided in the method step of provision of the error information. The error information in this case specifies that the process section determined is incorrect. In this case the process section determined is classified as incorrect if there is a probability greater than a threshold value that it is incorrect. The threshold value can for example be 68.3% or 70% or 80% or 85% or 90% or 95% or 95.4% or 99% or 99.7%.

In particular the data streams expected for a process section can be predefined by blacklisting or whitelisting. A blacklisting specifies which data streams are not expected during a process section determined. A data stream provided that is comprised by such a blacklist indicates that the process section provided is possibly incorrect. A whitelist specifies the data streams that are expected during the process section determined. In this case a data stream provided that is not comprised by the whitelist indicates that the process section determined is possibly incorrect.

For example the process section determined can be "introduction of the anesthetic". When during this process section x-ray images from the C-arm system are provided in the form of a data stream, this can indicate that the process section has been determined incorrectly, since typically x-ray images are not yet being recorded during the introduction of the anesthetic.

The error information can in particular initiate a new determination of the process section. As an alternative or in addition the error information can notify the operating personnel visually or audibly that the process section determined is possibly incorrect.

The inventors have recognized that, based on the data streams provided, it can be checked whether the process section determined is sensible. The inventors have recognized that it can thus be checked whether the expectation as regards the process and its progress matches the reality. In this case this check is independent of whether all data streams possible in the process section determined are provided. It is merely analyzed whether data streams are provided that are not expected during the process section determined.

According to an optional aspect of an embodiment of the present invention, error information is output when a particular data stream specific for the process section determined is not provided.

The error information can be embodied in this case as described above.

In this case at least one data stream is known for the process section determined that is always provided during the process section determined. In other words this data stream is provided independently of institution and/or independently of personnel and/or independently of country. In this case it is recognized that the process section determined is incorrect when this at least one process section is not provided.

The inventors have recognized that the process section determined can also be checked by a check being made as to whether at least the data streams expected in the process section determined are provided.

What is more, according to a further aspect of an embodiment of the present invention, the method comprises a method step of correction of the process section determined as a function of the data streams provided.

In particular the process section can be corrected in such a way that all data streams expected are also actually provided during the corrected process section. During correction, in versions of example embodiments of the present invention, in addition to the data streams provided, the overview data stream as described above can be taken into account.

In particular the method step of correction of the process section determined is carried out when error information is provided. In other words the method step of correction of the process section determined is carried out when it is recognized that the process section determined was determined incorrectly. The method step of correction of the process section determined can be triggered in this case by the error information. In other words the error information can be embodied in such a way that the method step of correction of the process section determined is initiated.

The inventors have recognized that in particular, when the current process section can only be determined without any certainty based on the overview data stream, a correction as a function of the data streams provided is possible. The inventors have recognized that the correct process section can be determined with great certainty in particular with a combination of the overview data stream and data streams provided.

According to a further aspect of an embodiment of the present invention, the data streams provided are dependent on the institution in which the process is carried out.

As already described above different data streams can be provided during the process for different institutions for the same process section. The reason for this can for example be the equipment of the institution. For example it is possible that not all institutions have an optical camera with which an overview of the process can be shown.

As an alternative or in addition the data streams provided can be dependent on the operating personnel carrying out or executing the process, for example the operation team. In other words the data streams provided can be specific to people. For example in one operation team a member can give voice commands while in another operation team no voice commands are given.

As an alternative or in addition data streams provided can be specific to a country. For example the data streams provided can differ in different countries due to data protection guidelines.

The inventors have recognized that for many reasons the data streams provided can be different for different institutions. The inventors have recognized that the method described can react flexibly to these differences. In this case the method adapts itself automatically to the circumstances, since the data streams that are evaluated are those actually provided. It is not necessary to adapt the method manually to the different circumstances at different institutions or even to different operating personnel or different people or operation teams.

According to a further aspect of an embodiment of the present invention, in each process section one of the individual classifiers is a base classifier. In this case to data stream to which the base classifier is assigned is provided in each institution. In this case the other data streams of the plurality of data streams expected in the process section are provided depending on the institution.

In this case the base classifiers can be at least partly different for different process sections.

In particular the base classifier is specific for the process. Different processes can have different base classifiers.

The data stream to which the base classifier is assigned is thus provided independently of the institution, the operating personnel and/or the country.

In versions of example embodiments of the present invention, more than one individual classifier in the process or per process section can be a base classifier. In other words more than one data stream can be provided independently of the institution during the process section or during the process.

In particular all other data streams to which no base classifier is assigned can be dependent on institution.

The inventors have recognized that frequently specific data streams are always acquired, in other words independent of institution or independent of people or independent of country, at least during a process section determined. The inventors have recognized that the individual classifier assigned to such a data stream can be classified as a base classifier. This base classifier can thus be applied in each institution, in each set of operating personnel and/or in each country to the corresponding data stream. The inventors have recognized that at least with this first base classifier a first estimation of the current or of the next working step is always possible. The inventors have recognized that this estimation can be optimized under some circumstances by taking into account the other data streams. In any event it is at least ensured by the base classifier and by the data stream assigned to it that an estimation for the current or next working step is always possible. The base classifier can thus always also be made available by default to each institution. The base classifier, for each institution, each country and/or each member of the operating personnel, thus ensures at least a basic functioning of the method.

According to a further aspect of an embodiment of the present invention, the individual classifiers are each trained individually centrally and/or in the institution in which the process is being carried out. Thus the locations of the training can be different for different individual classifiers.

Central training means in this case that a centrally trained individual classifier is trained centrally for all institutions. In particular the corresponding individual classifier can be trained centrally for all countries. To do this, training data streams or training data are transmitted from different institutions to a central memory, for example a central database. This central memory can for example be realized in a Cloud system. The central memory can be central for the whole world of at least for one country or for a group of countries. The individual classifier can then be trained centrally on this collected data.

As an alternative or in addition country-specific data protection guidelines can predetermine that specific data streams are not permitted to leave the corresponding country. For example corresponding data streams must be stored on servers that are arranged or positioned in the corresponding country. In such a case central training of the individual classifier assigned to such a data stream is only possible within the country determined. Then, where necessary, the corresponding individual classifier must be trained centrally individually for each country or each group of countries.

Training in the institution means that the corresponding individual classifier is trained locally on site in an institution. In this case the training data streams are data available in the institution. The training data streams thus do not "leave" the institution for training of the individual classifier.

In particular the location of the training of an individual classifier can depend on the data stream to which it is assigned. Many data streams, in particular for medical processes, are not provided for central processing and thus for central training due to data protection guidelines or data protection specifications. In other words many data streams are not permitted to leave an institution or a network of the institution due to data protection guidelines. Then the individual classifier assigned to such a data stream can only be trained at the institution itself.

In particular the central training and the training in the institution can be combined. In other words a combination of a central training and a training in the institution is possible.

For example an individual classifier can be centrally pre-trained. Subsequently the pre-trained individual classifier can be retrained in the institution, in which it is then to be used. In this way the individual classifier can be adapted to institution-specific circumstances without the data of the institution having to leave the institution and be stored centrally.

As an alternative an individual classifier can be pre-trained with data that is not permitted to leave an institution in said institution. This pre-trained individual classifier can subsequently be retrained centrally on freely available training data streams.

The inventors have recognized that, due to the independence of the individual classifiers, the training of the individual classifiers can be adapted, depending on the corresponding data streams, to the different data protection guidelines. In this way it is possible to adapt the training of the different individual classifiers to an availability of training data streams. What is more the inventors have recognized that, by a combined training, initially the knowledge from a large volume of training data streams can be used in order to pre-train the corresponding individual classifier. Subsequently the pre-trained individual classifier trained in this way can be retrained for the specific institution. In this way the individual classifier can be adapted to institution-specific circumstances. The inventors have recognized that in this way even training of an individual classifier for a specific person or for specific operating personnel is possible.

According to a further aspect of an embodiment of the present invention, the at least one individual classifier is centrally pre-trained and is continuously retrained in the institution.

The central training is embodied in this case as described above. For retraining the at least one individual classifier can be retrained for example based on feedback of a member of the operating personnel or of a person carrying out the process, for example at least one member of the operation team. In this case the least one parameter of the at least one individual classifier can be adapted in such a way that a result provided by the individual classifier, thus in particular the probabilities described above, matches the feedback especially well or leads to improved feedback.

The continuous retraining can thus be institution-specific and/or even person-specific.

The inventors have recognized that it is possible to continuously retrain the individual classifier in the institution even during the application of the individual classifier in the described method. The inventors have recognized that in this way the individual classifier can be continuously optimized and improved. What is more in this way changes, due to technical progress in the process for example, can be investigated and the individual classifier adapted accordingly.

According to a further aspect of an embodiment of the present invention, a classification result provided by one of the individual classifiers is used for supervised training of another individual classifier in the institution.

In other words the retraining in the institution can be embodied like a cascade. For this an individual classifier is first applied to the data stream to which it is assigned. In this case, as described above, at least one probability is determined for each working step of the list. These probabilities are referred to jointly with the corresponding working steps of the list as the classification result of the individual classifier. This classification result can then be used for supervised training of another individual classifier. In this case the other individual classifier is applied to the data stream to which this individual classifier is assigned. In this case both data streams originate from the same process and have been acquired in parallel in time during the process. By the application of the other individual classifier probabilities are likewise created for the working steps of the list. These are reconciled or compared during training with the previously determined classification result. Depending on this comparison the at least one parameter of the individual classifier to be trained is adapted in such a way that, with a renewed application of the adapted individual classifier to the corresponding data stream, the probabilities determined are a better match with the classification result.

In this case the training of the individual classifier can take place continuously during the application of the method. As an alternative the training can take place in a separate training method. Then the data streams to which the individual classifiers are applied during the training are in particular training data streams or training data.

The inventors have recognized that in this way an individual classifier can be trained within an institution without additional manual annotation of training data streams. The inventors have recognized that an individual classifier, which for example can be trained or pre-trained centrally, can serve as the basis for the training of an individual classifier that can only be trained within an institution. The inventors have recognized that in this way the training can be simplified for the individual institutions.

According to a further aspect of an embodiment of the present invention, the control signal is embodied for controlling a medical system and/or for an indication for operating personnel.

In this case the system described above is in particular a medical system. The medical system can for example be a medical imaging system and/or a monitoring system or an endoscope or a robotic system etc. The medical imaging system can in particular be a C-arm system but also a conventional x-ray system, a mammography system, an angiography system, a computed tomography system, a magnetic resonance tomography system, an ultrasound system etc. The control signal can thus be provided to the medical system. The control signal can then be embodied in such a way that the medical system, as a function of the control signal, carries out the current or the next working step. In other words the control signal can be embodied for control of the medical system. As an alternative the control signal can be a kind of trigger signal that triggers or initiates the current or the next working step at the medical system.

As an alternative or in addition the control signal can be embodied to be indicated to the operating personnel carrying out the process, for example to the operation team. In other words the control signal can be embodied to request that the operating personnel carry out the current or next working step. The control signal can be indicated on a screen in this case. The control signal can for example be indicated in this case in the form of a cue or a pictogram. The control signal can inform the operating personnel about which working step is being or is to be carried out as the current or next step. In particular the control signal can for example warn the operating personnel that the C-arm system is being moved and/or an x-ray image is being acquired. Then the operating personnel can move away from the C-arm system so as not to be injured during the movement and/or in order to minimize a dose for the operating personnel applied during acquisition of the x-ray image. As an alternative or in addition the control signal can request the operating personnel to carry out a next working step. For example the control signal can read "dilation of the stent" when it has been recognized that the stent is correctly positioned. The dilation can then be carried out manually following the control signal.

The inventors have recognized that through the control signal the process can both be controlled technically and also the operating personnel, in particular the operation team, can be informed at any time about progress of the process and can be instructed accordingly.

According to a further aspect of an embodiment of the present invention, the control signal comprises information about how long the current or the next working step lasts.

In particular the duration of the working step can be based on experience that specifies how long the corresponding working step typically lasts.

In this case the duration can be determined as an additional result during application of the individual classifiers to the corresponding data streams for the working steps of the list. When the individual classifiers are retrained as described above for a specific institution the duration can also be adapted to the institution and/or even to the person or system carrying out the corresponding working step.

The inventors have recognized that it is important for the planning of the process to know how long the current or the next working step (still) lasts. The inventors have recognized that then the system that is to carry out the next working step can be prepared in good time. As an alternative, when the next working step is carried out manually, the corresponding operating personnel can make themselves ready for carrying out the working step.

According to a further optional aspect of an embodiment of the present invention, the control signal specifies by whom or what the current or the next working step is carried out.

This information can be determined similarly to the way described above with regard to the duration either based on experience or by a corresponding adapted training of the individual classifiers.

The inventors have recognized that in this way a preparation of the system that is to carry out the current or next working step, or of the corresponding operator can be optimized. In this way pauses between the individual working steps can be prevented.

According to a further aspect of an embodiment of the present invention, each of the individual classifiers is assigned a confidence value and a threshold value. In this case the method step of determination of the current or next working step comprises a method step of determining the working step for which the greatest probability was determined with the individual classifier with the greatest confidence value. When this probability exceeds the threshold value of the corresponding individual classifier, the working step determined is the current or the next working step. When this probability falls below the threshold value of the corresponding individual classifier or is equal to the threshold value, the method step of determination of the current or next working step is repeated iteratively for the individual classifier with the next smallest confidence value until such time as the probability of the working step determined in this way exceeds the threshold value assigned to the corresponding individual classifier.

In particular the individual classifiers can be arranged in an order based on the respectively assigned confidence values. In this case the individual classifiers are arranged using the assigned confidence values in an order from the individual classifier with the greatest confidence value to the individual classifier with the smallest confidence value. When the same confidence value is assigned to two or more individual classifiers the corresponding individual classifiers can be put into an order manually or at random.

The confidence value in this case describes an importance or an informativeness of the corresponding individual classifier. The greater the confidence value, the more important or the more informative is the corresponding individual classifier in determination of the control signal. For example a maximum confidence value can be assigned to a data stream of a sound recording, in particular a data stream of a speech command. In this way it can be ensured that an intervention by the operating personnel has a maximum weighting.

The confidence values can be arranged in any given range of values. In particular the confidence values can be arranged in a range of values greater than or equal to 0 and less than or equal to 1 [0, 1].

The threshold value of an individual classifier specifies a probability. The threshold value specifies how great the probability for a working step that is determined by application of the individual classifier, must at least be so that the working step is determined as the current or next working step. Each individual classifier in this case is assigned such a threshold value. The threshold values of any two given individual classifiers can be different or the same.

The confidence value and the threshold value can be defined manually or automatically in advance. The confidence value and/or the threshold value can be adapted in any given way at any time.

In the method step of determination of the current or the next working step, first of all the individual classifier with the greatest confidence value is applied to the data stream assigned to the individual classifier. In this case a probability is determined for each working step of the list as described above.

In the method step of determination of the working step for which the greatest probability is determined with the individual classifier with the greatest confidence value, the working step from the list is determined for which the greatest probability was determined.

When this probability exceeds the threshold value that is assigned to the individual classifier, this working step is also determined as the current or next working step.

When the probability for the most probable working step is less than or equal to the threshold value, the method step described above of determination of the working step for which the greatest probability was determined is determined with the individual classifier with the second greatest or the next smallest confidence interval. For this the individual classifier to which the next smallest confidence interval is assigned is applied to the data stream assigned to it and once again a probability is determined for each working step of the list. As described above the working step is then determined for which the probability determined is the greatest. If this probability exceeds the confidence value assigned to the individual classifier this working step is determined as the current or the next working step. Otherwise the method step is repeated again for the individual classifier to which for its part the next smaller confidence value is assigned.

This process or this method step is repeated until such time as a probability of the most probable working step exceeds the threshold value of the corresponding individual classifier.

When this case does not arise for any of the individual classifiers or for any of the data streams provided, the working step for which, overall with all individual classifiers the greatest probability was determined, can be determined as the current or the next working step. In this case the "greatest probability for all individual classifiers" can mean that the probability on average is maximum for all data streams for the working step, or that the probability is the maximum probability for the corresponding working step from all probabilities determined.

As an alternative, when none of the probabilities determined exceeds the respective threshold value, the current or next working step can be determined via summed weighted probabilities as described further below.

In a similar way, when the greatest probability occurs multiple times, thus when the same greatest probability is determined for more than one working step, the current or next working step can be determined via summed weighted probability as described further below.

In versions of an embodiment of the present invention, both the current and the next working step can be determined in this way when, as described above, two probabilities are determined for each working step and each data stream by application of the individual classifiers to the data streams. In particular in this case the individual classifier can be assigned two threshold values: one threshold value for the current and one threshold value for the next working step. The method can then be carried out separately for the current and for the next working step separately. In this case the individual classifier with which the next working step is ultimately determined, and the individual classifier with which the current working step is ultimately determined can be different.

The inventors have recognized that the most suitable individual classifier for determination of the current or next working step can be determined by the combination of the confidence value and the threshold value.

According to a further aspect of an embodiment of the present invention, the threshold value for each individual classifier depends on the current process section.

In other words an individual classifier can be assigned a threshold value for each possible process section. In this case the threshold values can be different or the same.

The inventors have recognized that it can be taken into account by different threshold values in different process sections that an individual classifier for different process sections can be differently well suited to determining the current or next working step. When the threshold value is especially large an individual classifier with a large confidence value must predict the working step with a correspondingly large probability, whereby it can be ensured that the current or next working step can also be determined as such with sufficiently great certainty.

According to a further aspect of an embodiment of the present invention, each of the individual classifiers is assigned a confidence value. In this case the method step of determination of the current or next working step comprises a method step of multiplication of the probability determined for each working step by the confidence value of the corresponding individual classifier. In this case a weighted probability is determined for each working step, depending on the individual classifiers. In this case the method step of determination of the current or next working step comprises a method step of addition of the weighted probabilities of the different individual classifiers for each working step. In this case a summed weighted probability is determined for each working step. In this case the working step for which the summed weighted probability is the greatest is determined as the current or next working step.

The confidence values assigned to the individual classifiers are embodied as described above.

As described above, a probability is determined by application of the individual classifiers to the data streams assigned for each working step of the list in each case. In other words in this case, for each working step and each data stream, a probability is determined for the corresponding working step being the current or the next working step.

All probabilities that are determined with an individual classifier, which are thus determined by application of the individual classifier to the assigned data stream, are multiplied by the confidence value assigned to the individual classifier. This is carried out in the method step of multiplication of the probabilities for each working step for each individual classifier. In this way weighted probabilities are determined with the corresponding confidence values.

In the method step of addition of the weighted probabilities the weighted probabilities determined as described above that were determined for the same working step with different individual classifiers are added. In this way an added weighted probability is determined for each working step of the list.

A NaN value or a default value for a probability for a working step is handled in the method step of multiplication and in the method step of addition like a 0% probability.

The working step for which the greatest of the summed weighted probabilities can be determined in this way is then the current or the next working step.

When the same greatest summed weighted probability is determined for more than one working step, that working step from these working steps is determined as the current or next working step for which the greatest probability was determined with the individual classifier with the greatest confidence value.

This method can be carried out separately for determination of the current and the next working step based on the two probabilities determined as described above for the current and the next working step.

The inventors have recognized that in this way it can be taken into account that the different individual classifiers can be differently good for determination of the current or the next working step. The inventors have recognized that by the weighting or the multiplication or the addition it is still ensured that, independent of which data stream is provided, a current or next working step can still be determined. The inventors have recognized that by the weighting or the multiplication or the addition a poorly suited individual classifier, i.e. an individual classifier to which in this case a low confidence value is assigned, can be prevented from having a great influence on the determination of the current or the next working step if only a few data streams are provided. In particular it can on the other hand be taken into account in this way when a data stream or an individual classifier is especially well suited.

According to a further aspect of an embodiment of the present invention, the confidence value for the individual classifiers depends on the process section.

In other words a confidence value can be assigned to an individual classifier for different process sections in each case. The assigned confidence values can be different or the same at least in part.

The inventors have recognized that in this way it can be taken into account that an individual classifier can be differently well suited for application in different process sections.

According to a further aspect of an embodiment of the present invention, the method step of determination of the current or next working step comprises a method step of application of a trained function to the probability determined for each working step and each individual classifier. In this case the current or next working step is determined.

The trained function can be embodied in this case as generally described above. In particular the trained function can have been trained via supervised training. The trained function is embodied to receive the probabilities determined for the different individual classifiers and the different working steps as input data. The trained function then determines from this input data the working step that is the current or the next working step. In particular the trained function can determine the current and the next working step. In this case the trained function can be applied separately or combined to the two probabilities that were determined for each individual classifier and each working step.

The inventors have recognized that the correct current or next working step can be determined by a trained function. The inventors have recognized that the trained function can be embodied to deal with variable input data due to the variable data streams provided.

What is more, according to a further aspect of an embodiment of the present invention, the method comprises a method step of determination of a selection of individual classifiers from the plurality of individual classifiers for the current process section as a function of the data stream. In this case, in the method step of application of the individual classifiers, the selection of the individual classifiers is applied to the corresponding selection of data streams provided.

In particular, by the determination of the selection of individual classifiers, especially suitable individual classifiers can be determined for the current process section. In this case it is taken into account which data streams are provided and which individual classifiers are thus relevant. In other words a selection of data streams that describes the current process section especially well is determined from the data streams provided. An individual classifier that is not assigned to any of the data streams provided is not taken into account in the selection of the individual classifiers.

The selection of individual classifiers in this case comprises at least one individual classifier. When only one data stream is provided, the selection comprises the individual classifier assigned.

In particular the selection can for example be based on the assigned confidence values. In this case the individual classifiers can be selected of which the assigned confidence value is greater than or equal to a predetermined confidence value. When no individual classifier that is assigned to a data stream provided is greater than or equal to the predetermined confidence value, at least the individual classifier with the greatest confidence value can be selected.

In the method step of application of the individual classifiers the selection of individual classifiers is then applied to the corresponding assigned data streams. When further data streams are provided of which the assigned individual classifiers are not comprised by the selection, these data streams are no longer considered for the current process section.

The inventors have recognized that computing power that is needed can be reduced and thus carrying out the method described can be speeded up by the selection of the individual classifiers. In other words in this way it can be ensured that only the actually relevant individual classifiers are applied. For example a monitoring system not connected can provide a data stream even when the examination object is currently being monitored by a heart-lung machine. This data is then unusable, since for example the heart of the examination object is not beating at that moment. Since it is known that in such a case or in such a process section the data stream provided by the monitoring system is not informative, the correspondingly assigned individual classifier is not selected. In particular a low confidence value, in particular a confidence value of 0 can be assigned to the individual classifier for the corresponding process section in which the heart-lung machine is connected. The inventors have recognized that then such an individual classifier does not have to be applied to the corresponding data stream. The computing power that the application of the individual classifier to the correspondingly assigned data stream would need can thus be saved. What is more the inventors have recognized that in particular the cascade-like evaluation or analysis described above of the probabilities determined by the different individual classifiers as a function of the correspondingly assigned confidence values and threshold values can be speeded up when only the individual classifiers are applied and thus determine probabilities that are actually informative for determining the current or next working step.

According to a further aspect of an embodiment of the present invention, the data streams provided are data streams from the following data streams: fluoroscopy recordings, film recordings, ECG recordings, sound recordings, a user input, an item of system information.

The fluoroscopy recordings correspond to the x-ray recordings or x-ray images acquired as described above via fluoroscopy with a C-arm system. The fluoroscopy recordings are provided by the C-arm system. The overview data stream can in particular comprise the fluoroscopy recordings.

The film recordings can in particular be acquired with one or more optical cameras and be provided by these. The overview data stream can in particular comprise the film recordings.

The ECG recordings can be provided in particular by a monitoring system. ECG in this case is the acronym for electrocardiogram.

The sound recordings can be provided in particular by the operating personnel or the operation team. In other words a speech input of the operating personnel or the operation team is captured via a microphone and provided as a sound recording.

The user input describes an input of the operating personnel or the operation team. For example a member of the operating personnel can specify via an input unit which working step they are carrying out or which working step is just being or is to be carried out by the system. The input unit can for example be a keyboard, a computer mouse, a touchpad and/or a touch screen.

The system information can for example be a status of one of the systems. In other words the system information is provided by one of the systems. The system information can specify a state of the corresponding system. For example the system information can specify whether the system is currently in use or which working step the system is just carrying out or plans to carry out or whether the system is in a standby mode etc.

The inventors have recognized that the data streams can be a plurality of different data streams. The inventors have recognized that the different data streams can provide different information about the process. The inventors have recognized that the combination of the data streams provided can be used in order to determine the current or the next working step especially reliably.

What is more one or more example embodiments of the present invention relate to a computer-implemented method for provision of individual classifiers. In this case the method comprises a method step of provision of a training data stream to which the individual classifier is uniquely assigned. What is more the method comprises a method step of provision of a list comprising a plurality of working steps, wherein each working step of the list is assigned a training probability, which specifies how probable it is that the corresponding working step is the current or the next working step. What is more the method comprises a method step of training the individual classifier based on the training data stream and the training probabilities. What is more the method comprises a method step of provision of the individual classifier.

The training data stream or the training data is embodied in this case like one of the data streams described above. In particular the process for which the training data stream is provided is already completed. The training data stream, for training of the individual classifier at a given point in time, can interrupt the process for which the current or next working step is to be determined by application of the individual classifier.

The list of working steps is likewise embodied as described above.

The training probabilities can in particular have been determined manually. For this one or more persons that are experienced in the process can manually determine the training data stream and in versions one or more other data streams that describe the process can be provided and the person can then determine the training probabilities manually.

As an alternative the training probabilities can be determined based on a further course of the process. For this the process that is described by the training data stream can already be completed. Thus it is known which working step, at the point in time at which the training data stream aborts, is actually being carried out as the current or the next. This knowledge can be used to determine the training probabilities.

As an alternative or in addition the probabilities determined with another already trained individual classifier can be assumed as the training probabilities for the different working steps as described above. For this the already trained individual classifier is applied to a data stream that has been acquired during the same process and in parallel in time with the training data stream. The probabilities determined in this case for the individual working steps are then assumed as the training probabilities.

In the method step of training the individual classifier is applied to the training data stream. In this case a probability is determined for each working step of the list, which specifies how probable it is that the corresponding working step is being carried out as the current or next step. These probabilities determined are compared with the training-probabilities. Based on this comparison at least one parameter of the individual classifier can be adapted in such a way that, when the individual classifier is applied once more to the training data stream, the probabilities determined better match the training probabilities.

These method steps can be carried out multiple times. In particular these method steps can be carried out for training data streams from different processes. In this case the training data streams are always provided by the same system provided. "The same" system means in this case that it is always the same type of system that is involved, for example always a C-arm system or always a monitoring system etc. As an alternative or in addition the training data stream can be aborted at different points in time during the process and the method steps repeated for the different points in time.

The method steps can be repeated until such time as a maximum number of repetitions have been carried out. As an alternative or in addition the method steps can be repeated until such time as the difference between the probabilities determined and the training probabilities falls below a predetermined maximum probability value.

This method can be carried out in a similar way for the different individual classifiers.

The individual classifier trained in this way can then be provided in the method step of provision of the individual classifier for use in the method described above.

The inventors have recognized that the individual classifiers can be trained via supervised training. The inventors have also recognized that other types of training, for example pure classification methods, are possible for determination of the individual classifier.

What is more one or more example embodiments of the present invention relate to a provision system for provision of a control signal for carrying out a current or next working step in a process. The provision system comprises an interface and a computing unit. In this case the interface is embodied for provision of a plurality of data streams. In this case the data streams provided depend on a process section of the process. In this case each of the data streams is uniquely assigned an individual classifier in each case. What is more the interface is embodied in this case for provision of a list comprising a plurality of possible working steps. In this case the computing unit is embodied for application of an individual classifier to the data stream assigned in each case. In this case each individual classifier, based on the data stream assigned in each case, determines for each working step a probability that specifies how probable it is that the corresponding working step will be carried out as the current or the next step. What is more in this case the computing unit is embodied to determine the current or next working step as a function of the probabilities determined. What is more in this case the interface is embodied for provision of the control signal for carrying out the current or next working step.

Such a provision system can in particular be embodied for carrying out the previously described method for provision of a control signal for carrying out a current or next working step and its aspects. The provision system is embodied to carry out this method and its aspects by the interface and the computing unit being embodied to carry out the corresponding method steps.

What is more one or more example embodiments of the present invention relate to a training system for provision of individual classifiers. In this case the training system comprises a training interface and a training computing unit. The training interface is embodied in this case for provision of a training data stream to which the individual classifier is uniquely assigned. The training interface is embodied in this case for provision of a list comprising a plurality of working steps. In this case each working step of the list is assigned a training probability that specifies how probable it is that the corresponding working step is the current or the next working step. The training computing unit is embodied for training the individual classifier based on the training data stream and the training probabilities. What is more the training interface is embodied for provision of the individual classifier.

Such a training system can in particular be embodied for carrying out the previously described method for provision of an individual classifier. The training system is embodied for carrying out this method by the training interface and the training computing unit being embodied for carrying out the corresponding method steps.

One or more example embodiments of the present invention also relate to a computer program product with a computer program and also to a computer-readable medium. A largely software-based realization has the advantage that even provision systems or training systems already used can be upgraded in a simple way by a software update in order to work in the way described. Such a computer program product, as well as the computer program, can where necessary also comprise additional elements such as e.g. documentation and/or additional components, and also hardware components, such as e.g. hardware keys (dongles etc.) for use of the software.

In particular, one or more example embodiments of the present invention relate to a computer program product with a computer program that is able to be loaded directly into a memory of a provision system, with program sections for carrying out all the steps of the method described above for provision of a control signal for carrying out a current or next working step and its aspects when the program sections are executed by the provision system.

One or more example embodiments of the present invention relate in particular to a computer-readable memory medium on which program sections able to be read an executed by a provision system are stored for carrying out all steps of the method described above for provision of a control signal for carrying out a current or next working step and its aspects when the program sections are executed by the provision system.

One or more example embodiments of the present invention also relate in particular to a computer program product with a computer program, which is able to be loaded directly into a memory of a training system, with program sections for carrying out all steps of the method described above for provision of an individual classifier when the program sections are executed by the training system.

One or more example embodiments of the present invention relate in particular to a computer-readable memory medium, on which program sections able to be read and executed by a training system are stored for carrying out all steps of the method described above for provision of an individual classifier and its aspects when the program sections are executed by the training system.

BRIEF DESCRIPTION OF THE DRAWINGS

The characteristics, features and advantages of this invention will become clearer and easier to understand in conjunction with the following figures and their descriptions. In this case the figures and descriptions are in no way intended to restrict the present invention and its forms of embodiment.

In different figures the same components can be provided with corresponding reference characters. As a rule the figures are not true-to-scale.

In the figures:

Figure 1:
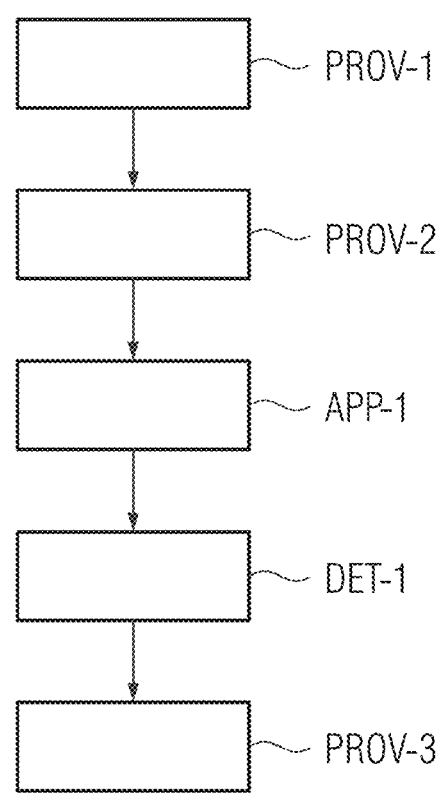
Figure 2:
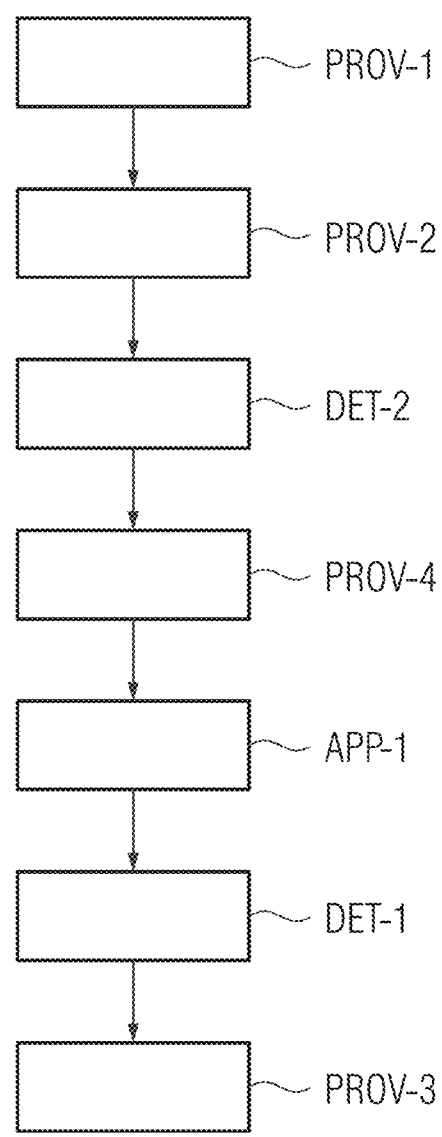
Figure 3:
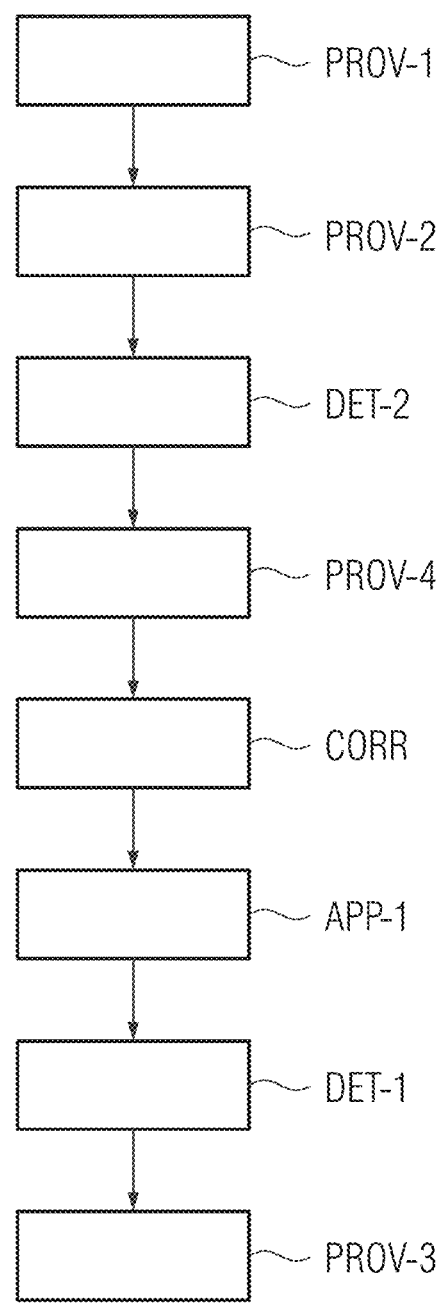
Figure 4:
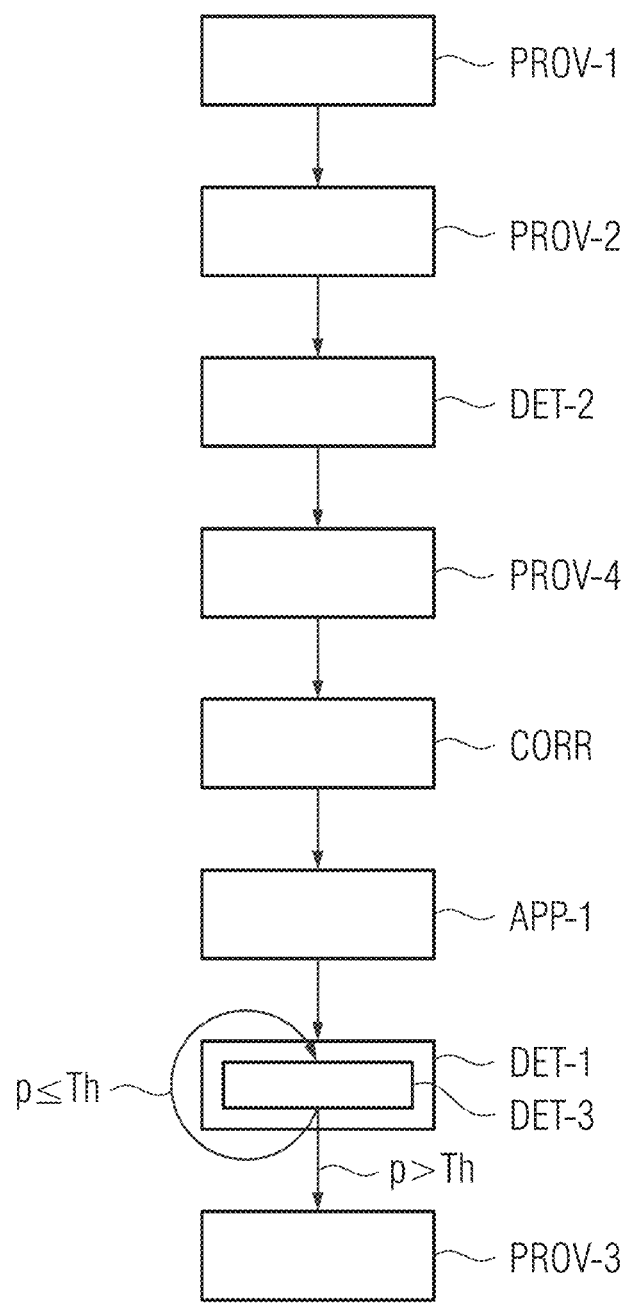
Figure 5:
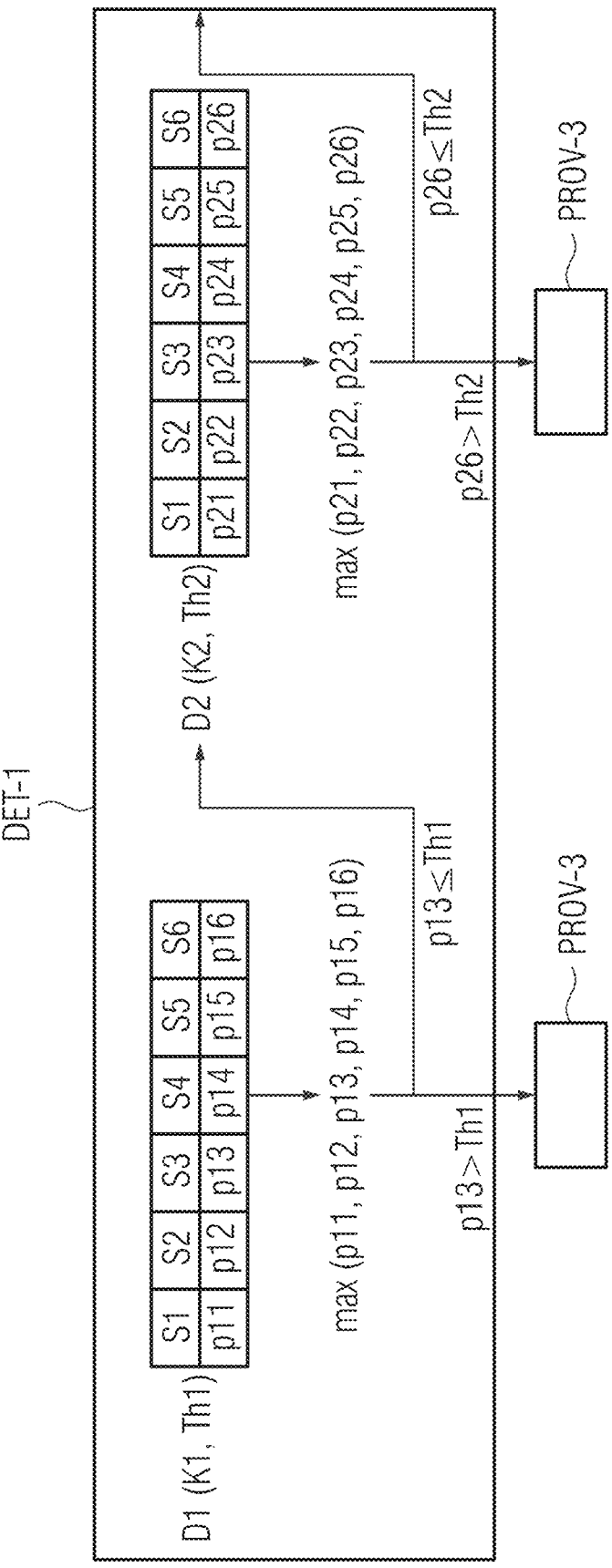
Figure 6:
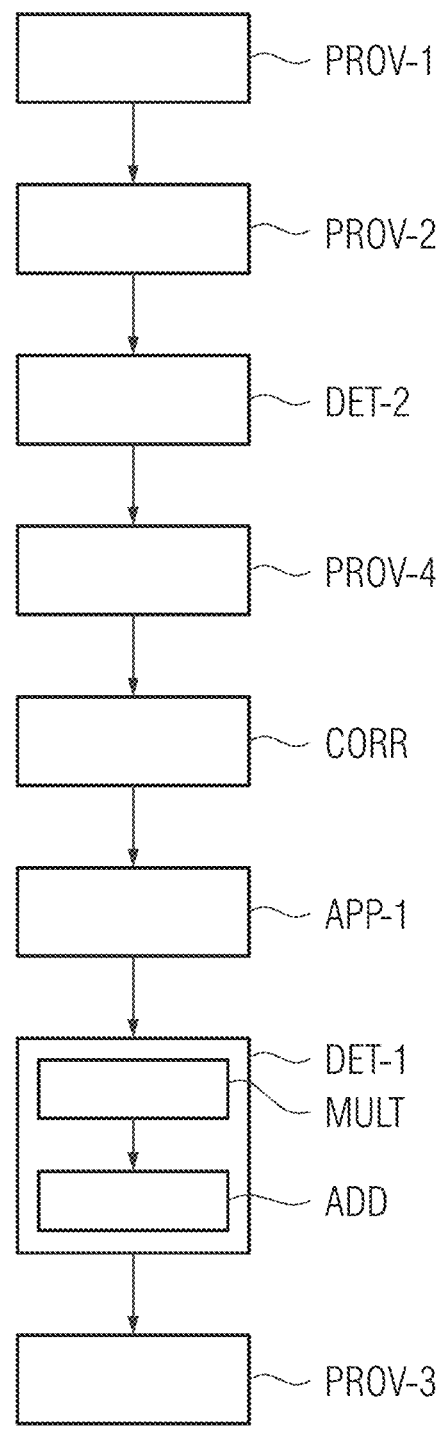
Figure 7:
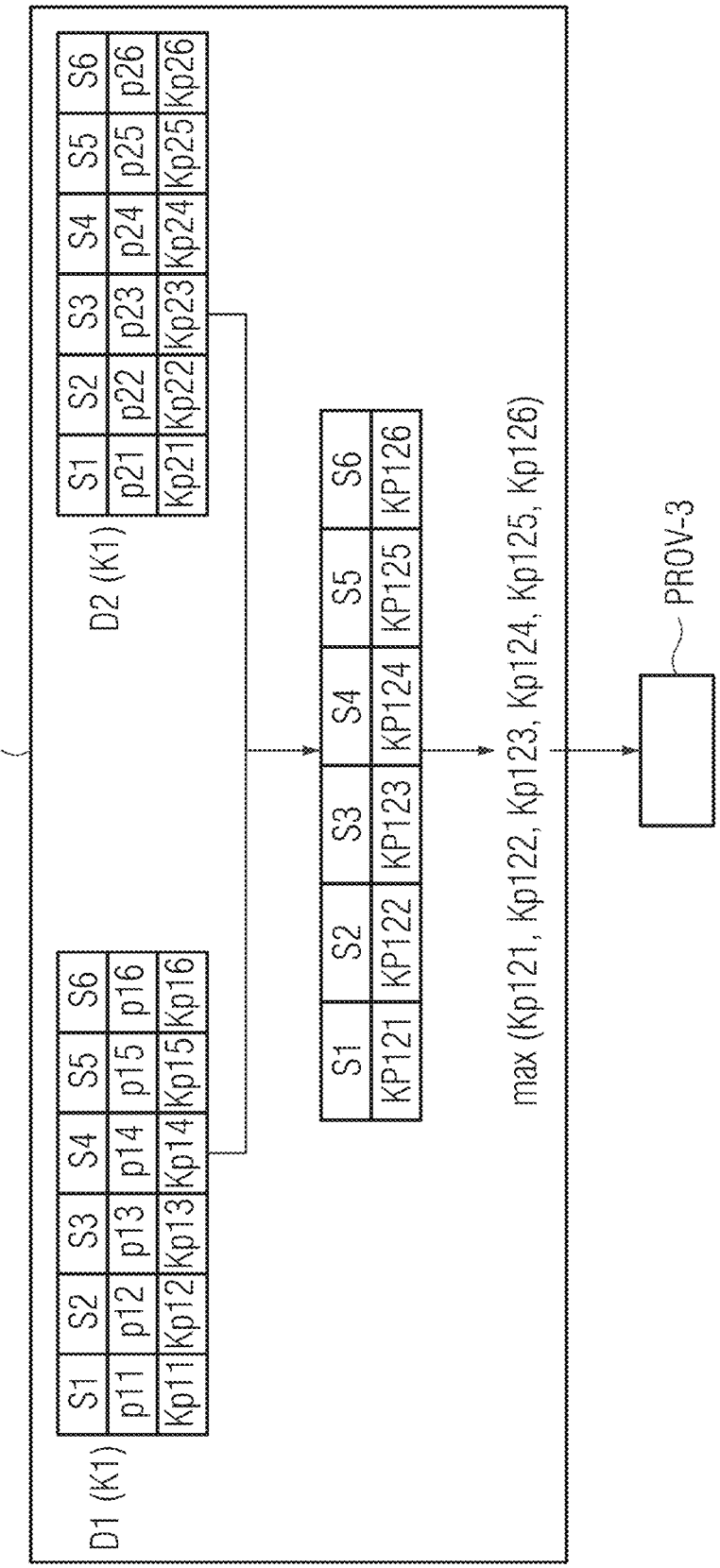
Figure 8:
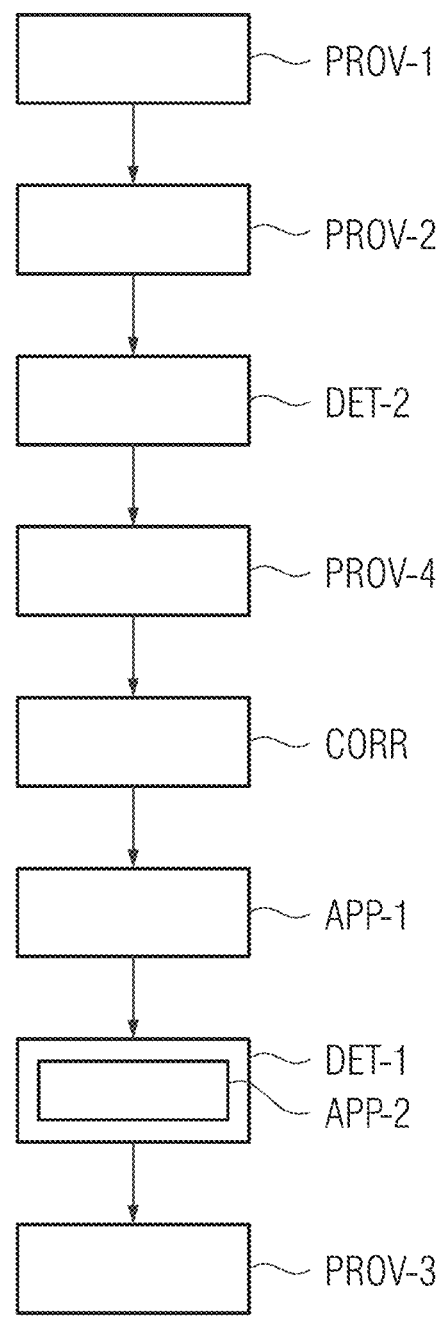
Figure 9:
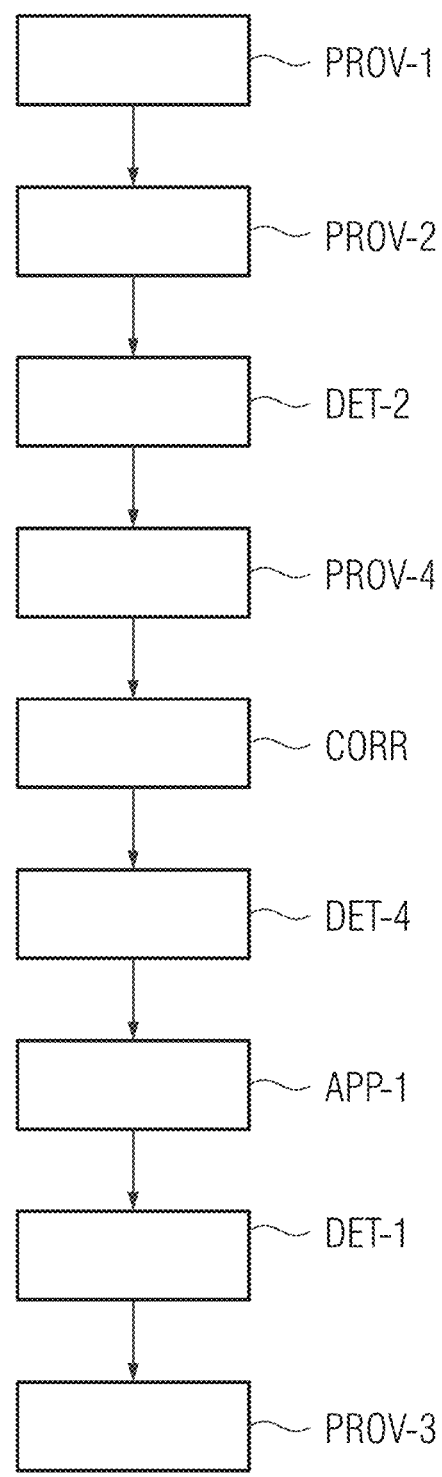
Figure 10:
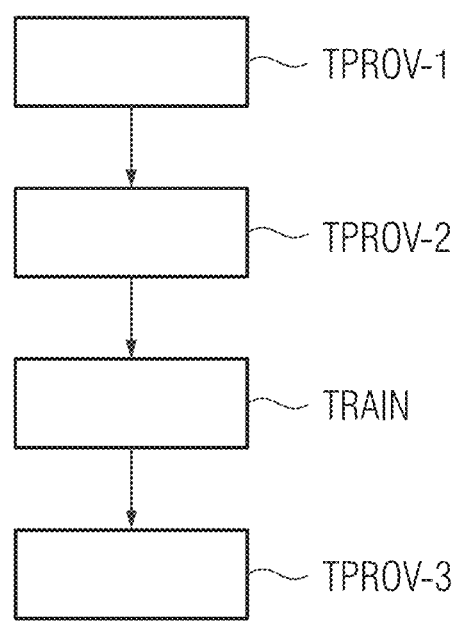
Figure 11:
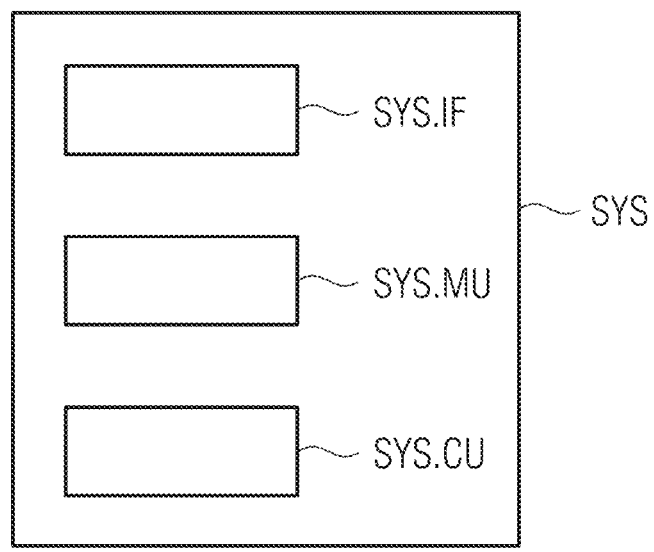
Figure 12:
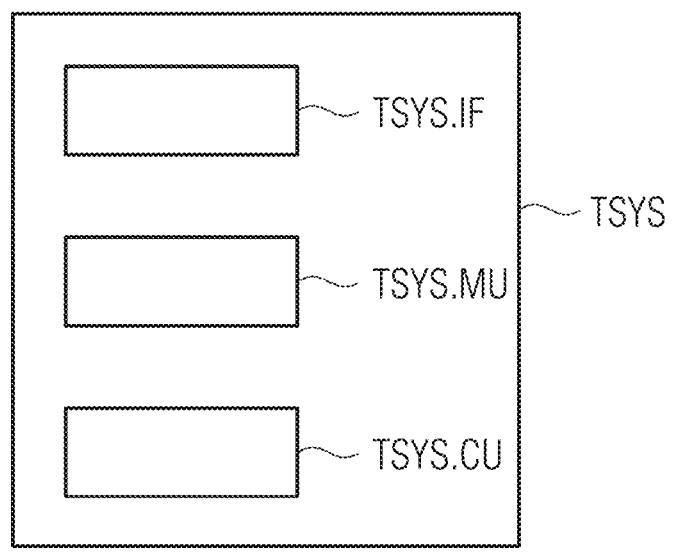

FIG. 1 shows a first exemplary embodiment of a computer-implemented method for provision of a control signal for carrying out a current or next working step, FIG. 2 shows a second exemplary embodiment of a computer-implemented method for provision of a control signal for carrying out a current or next working step, FIG. 3 shows a third exemplary embodiment of a computer-implemented method for provision of a control signal for carrying out a current or next working step, FIG. 4 shows a fourth exemplary embodiment of a computer-implemented method for provision of a control signal for carrying out a current or next working step, FIG. 5 shows a first exemplary embodiment of a method step of determination of a current or next working step, FIG. 6 shows a fifth exemplary embodiment of a computer-implemented method for provision of a control signal for carrying out a current or next working step, FIG. 7 shows a second exemplary embodiment of a method step of determination of a current or next working step, FIG. 8 shows a sixth exemplary embodiment of a computer-implemented method for provision of a control signal for carrying out a current or next working step, FIG. 9 shows a seventh exemplary embodiment of a computer-implemented method for provision of a control signal for carrying out a current or next working step, FIG. 10 shows an exemplary embodiment of a computer-implemented method for provision of an individual classifier, FIG. 11 shows a provision system for provision of a control signal for carrying out a current or next working step, FIG. 12 shows a training system for provision of an individual classifier.

DETAILED DESCRIPTION

FIG. 1 shows a first exemplary embodiment of a computer-implemented method for provision of a control signal for provision PROV-3 of a current or next working step S1, S2, S3, S4, S5, S6.

The current or next working step S1, . . . , S6 is comprised in this case by a process. In other words the current or next working step S1, . . . , S2 is carried out during the process. The process can in particular be a medical process. For example the medical process can be a medical intervention or a medical operation. The medical process can be carried out on an examination object, for example a human being or an animal. The process can in this case be carried out by a member of the operating personnel and/or by systems for supporting and/or monitoring and/or carrying out the process. In the case of a medical process the operating personnel can be an operation team.

The data streams D1, D2 are in particular received in a method step of provision PROV-1 of a plurality of data streams D1, D2. In this case the data streams D1, D2 are provided by a system supporting and/or monitoring and/or carrying out the process in each case. Such a system can for example be an x-ray system, in particular a C-arm system, a monitoring system, a camera system, a recording system for recording sound signals etc. The system can thus in particular be a medical system.

The data streams D1, D2 provided are suitable in this case for describing the process. This means that the data streams D1, D2 provided are at least suitable for describing a section of the process or a process section. In this case each of the data streams D1, D2 can describe at least one aspect of the process or of the process section. One aspect can for example be a state of the examination object during the process. Another aspect can for example be a placing of a stent when the process comprises a setting of a stent.

The data streams D1, D2 provided depend in this case on the current process section of the process. In other the words the data streams D1, D2 that are provided depend on the process section. The process in this case is divided into sections or process sections. The process sections can divide up the process thematically. With a medical process the process sections can for example be called "introduction of an anesthetic", "opening up of the examination object", "carrying out the operation", "sewing up the examination object" and "recovery from the anesthetic".

The data streams D1, D2 provided can also depend on an institution at which the process is being carried out or executed. In other words different institutions can provide different data streams D1, D2 for the same process sections. The reason for this can be different equipment for example.

As an alternative or in addition the data streams D1, D2 provided can depend on operating personnel who are carrying out the process. In particular the data streams D1, D2 provided can reflect the preferences of the operating personnel when carrying out the process.

As an alternative or in addition the data streams D1, D2 provided can depend on the country or a group of countries in which the process is carried out. Different countries or groups of countries can specify different standards that must be fulfilled when the process is being carried out. These can also relate to the systems used and thus to the data streams D1, D2 provided.

Each of the data streams D1, D2 is uniquely assigned an individual classifier.

In particular one or more data streams can also be provided to which no individual classifier is assigned. This data stream or these data streams are not relevant for the method and are not taken into further consideration below.

In versions of example embodiments of the present invention, in each process section one of the individual classifiers that is assigned to a data stream D1, D2 provided is a base classifier. The data stream D1, D2 to which the base classifier is assigned is provided independent of institution in the corresponding process section. In other words this data stream D1, D2 is always provided in the corresponding process section, independent of the institution, the country or group of to the operating personnel. Thus for each process section a base classifier is known that, as described below, can always be applied in the corresponding process section in order to determine the current or next working step S1, . . . , S6.

In a method step of provision PROV-2 of a list a list that comprises a plurality of possible working steps S1, . . . , S6 is provided.

The list can in this case comprise all possible working steps S1, . . . , S6 that can occur in a process of the given kind. For example the list, if it is provided for a medical process, can comprise all possible working steps S1, . . . , S6 that can occur in a given medical process.

As an alternative the list can comprise only those working steps S1, . . . , S6 that can also actually occur in the given process. In other words, by comparison with the previously described example, the list can be restricted to the working steps S1, . . . , S6 that are relevant for the process for which the method is to be carried out. When the process is a specific operation for example, then in this case the list comprises only working steps that can also actually be carried out during this operation.

As an alternative the list can be restricted to the working steps S1, . . . , S6 that can occur in the current process section. In other words the list comprises the working steps S1, . . . , S6 relevant for the current process section.

In particular the list can be processed in advance in such a way that it merely comprises relevant possible working steps S1, . . . , S6 for the process or for the current process section.

In a method step of application APP of the individual classifiers the individual classifiers are applied to the data streams D1, D2 to which they are assigned in each case. In this case, for each data stream D1, D2 and each working step S1, . . . , S6 of the list, a probability p, p11, p12, p13, p14, p15, p16, p21, p22, p23, p24, p25, p26 is determined that the corresponding working step S1, . . . , S6 will be the current or the next step carried out. A working step S1, . . . , S6, for which no probability can be defined is assigned a probability of 0% or a default value or NaN value in this case. Working steps S1, . . . , S6, to which a default or NaN value is assigned can be handled below like working steps S1, . . . , S6, for which a probability of 0% has been determined.

In particular two probabilities p, p11, . . . , p26 can be determined for each working step S1, . . . , S6 and each individual classifier in each case. In this case a probability p, p11, . . . , p26 specifies how probable it is that the corresponding working step S1, . . . , S6 is currently being carried out and the other probability p, p11, . . . , p26 specifies how probable it is that the corresponding working step S1, . . . , S6 will be carried out as the next step. The "or" regarding current or next working step S1, . . . , S6 refers here to a non-exclusive "or".

The individual classifiers can in particular be trained in each case specifically for the corresponding data stream D1, D2. In other words the individual classifiers are specifically embodied to be applied to the data stream D1, D2 assigned to them in each case. In this case the individual classifiers can have been trained independently of one another.

The different individual classifiers can be trained centrally and/or in the institution in which the process is carried out in each case.

When an individual classifier is trained centrally, training data streams or training data is collected centrally, on a central server, for example Cloud server. The training data streams for training of an individual classifier are embodied in a similar way to the data stream D1, D2 to which the individual classifier is able to be applied. In other words the training data streams are provided with the same system with which the data stream D1, D2 assigned to the individual classifier is also provided. In this case "the same" system does not necessarily mean that the identical system must be involved. It can also merely be that a system of the same type is involved. The same type in this case means for example that both the training data stream and also the assigned data stream are acquired with a C-arm system. In this case different C-arm systems in different institutions can be involved. Thus, for training in particular, training data streams from different institutions are collected centrally and the corresponding individual classifier is trained there centrally.

When an individual classifier is trained in the institution the training data streams must not leave the institution. The training data streams in this case are embodied as described above. However the corresponding individual classifier is only trained locally on the training data streams of the corresponding institution.

The location of the training of an individual classifier can in this case depend in particular on the data stream D1, D2 or the training data streams for training of the individual classifier. For example an individual classifier of which the training data streams, due to data protection guidelines for example, are not permitted to leave the institution, is trained in the institution while an individual classifier of which the training data streams are able to be collected centrally is trained centrally. The adaptation of the location of the training can thus in particular be suitable for fulfilling data protection guidelines.

In particular the central training and the training in an institution can be able to be combined. For example an individual classifier can be pre-trained on centrally available training data streams and subsequently retrained locally on the institution-specific training data streams. In this way on the one hand the data protection guidelines can be adhered to, on the other hand an institution-specific training is possible. The centrally pre-trained individual classifier can in this way be retrained for a specific institution and be adapted to special features of the institution.

As an alternative an individual classifier can also be pre-trained in an institution and subsequently retrained centrally.

An individual classifier can be continuously further trained during its use or application in an institution. Feedback of the operating personnel can be used for this in order to establish whether a result determined with the individual classifier was determined correctly. The individual classifier can be adapted during the continuous training in such a way that a result determined by application of the individual classifier matches the expectations in accordance with the feedback of the operating personnel especially well.

In particular only the individual classifiers are applied for which the assigned data stream is provided in each case. In this way the method can be adapted flexibly to the circumstances when the process is carried out. For example the method can be adapted flexibly to the institution or the operating personnel or the country or the group of countries in which or by which the process is carried out.

In a method step of determination DET-1 of the current or the next working step S1, . . . , S6 the current or the next working step S1, . . . , S6 is determined as a function of the probabilities p, p11, . . . , p26 determined. In this case account can be taken of which probability p, p11, . . . , p26 was determined, as a function of which data stream D1, D2 or of which assigned individual classifiers assigned to this.

In a method step of provision PROV-3 of the control signal the control signal for carrying out the current or next working step S1, . . . , S6 is provided.

In this case the control signal can be provided to a system that is to carry out the current or the next working step S1, . . . , S6. The system that is to carry out the current or next working step can in this case be none of the systems that have provided one of the data streams D1, D2. As an alternative the system that is to carry out the current or next working step can be comprised by the systems that provide the data streams. In particular the control signal S1, . . . , S6 can be embodied in such a way that the corresponding system carries out the working step S1, . . . , S6 as a function of the control signal. As an alternative the control signal can be embodied in such a way that the current or the next working step S1, . . . , S6 is initiated at the system. In other words the control signal can be embodied to trigger or to initiate the current or next working step S1, . . . , S6 at the system. In other words the control signal can be embodied to control the system, in particular a medical system. In this case the control signal can be adapted to the system that is to be controlled by the control signal.

As an alternative or in addition the control signal can inform the operating personnel about the current or next working step S1, . . . , S6. In other words the control signal can be embodied to request the operating personnel to carry out the current or next working step S1, . . . , S6. In particular the control signal can be indicated on a screen or monitor. In this case the working step S1, . . . , S6 can be described in the form of a cue or of a pictogram. As an alternative or in addition the control signal can be provided to the operating personnel via an acoustic output. The control signal provided to the operating personnel can specify which working step S1, . . . , S6 will be carried out as the current or the next step. In addition the control signal can specify who or what is to carry out the current or next working step S1, . . . , S6. In other words the control signal can specify by whom or by what the corresponding working step S1, . . . , S6 is to be carried out. In particular the control signal can be embodied in such a way that the operating personnel is requested by the provision PROV-3 to carry out the current or next working step S1, . . . , S6.

In versions of example embodiments of the present invention, the control signal can comprise information about how long the current or the next working step S1, . . . , S6 lasts. This information can likewise be determined by application of the individual classifiers to the assigned data stream D1, D2 in each case. In particular the duration can be indicated to the operating personnel. In versions of example embodiments of the present invention, a "remaining time" of the current working step S1, . . . , S6 can be indicated to the operating personnel. In other words it can be indicated when the current or the next working step S1, . . . , S6 begins.

What is more, in versions of example embodiments of the present invention, the control signal can specify by whom or what the current or the next working step S1, . . . , S6 is to be or is carried out. In other words the control signal can specify which system is to carry out the current or next working step S1, . . . , S6. As an alternative the control signal can specify when the current or the next working step S1, . . . , S6 is to be carried out manually.

In versions of example embodiments of the present invention, an individual classifier can be trained as a function of one or more other individual classifiers. In this case an individual classifier can already be trained. As described above, by application of the already trained individual classifier to the corresponding data stream or to the corresponding training data streams D1, D2 assigned to it, training data probabilities p, p11, . . . , p26 are determined. These probabilities p, p11, . . . , p26 are referred to below as the classification result. Another individual classifier to be trained can likewise be applied to the data stream D1, D2 or training data streams assigned to it. In this case probabilities p, p11, . . . , p26 are likewise determined. These probabilities p, p11, . . . , p26 are compared with the classification result. In this case the individual classifier to be trained is adjusted in such a way that the probabilities p, p11, . . . , p26 determined with this individual classifier match the classification result of the already trained individual classifier as well as possible. In this case in particular the probabilities p, p11, . . . , p26 of the two individual classifiers determined for two of the same working steps S1, . . . , S6 should match. The data streams D1, D2 or the training data streams to which the two individual classifiers are applied are advantageously acquired at the same time or in parallel or at least during the same process section with the different system.

FIG. 2 shows a second exemplary embodiment of a computer-implemented method for provision PROV-3 of a control signal for carrying out a current or next working step S1, . . . , S6.

The method steps described in the description for FIG. 1 of provision PROV-1 of a plurality of data streams D1, D2, of provision PROV-2 of a list, of application APP-1 of the individual classifiers, of determination DET-1 of the current or next working step S1, . . . , S6 and of provision PROV-3 of the control signal are embodied in a similar way to the description.

The method comprises a further optional method step of determination DET-2 of the process section as a function of an overview data stream.

The overview data stream is embodied to map or to represent a general aspect of the process. In particular the overview data stream is embodied to provide an overview or an oversight of the process. The overview data stream is provided in this case during the process as a whole. In this case the overview data stream can be provided continuously or with interruptions. For example the overview data stream can be provided during the process as a whole at determined intervals or in determined time windows.

The overview data stream in this case can be provided for example by a camera filming the process and/or via fluoroscopy. The camera in this case can be an optical camera, in other words a video camera, which provides temporally resolved image data. The camera can be arranged in this case in such a way that it shows an overview of the process, thus of the examination object, the operating personnel and/or the systems. In this case the camera can comprise more than one camera element, wherein each of the camera elements films the process from a different perspective. The fluoroscopy is a temporally resolved acquisition of x-ray images of the examination object with a C-arm system.

When the overview data stream is provided via fluoroscopy, the process does not comprise any preparatory and subsequent processing steps, such as for example the introduction of and recovery from the anesthetic.

The process section or the current process section can thus be determined as a function of the overview data streams. For example the process section can be determined by application of a trained function to the overview data stream. In this case the trained function can for example be based on pattern recognition.

In a further optional method step of provision PROV-4 of error information the error information is provided, which specifies that the process section determined is incorrect when a data stream D2, D2 is provided that is not expected in the process section determined.

In this case it is known which data streams D1, D2 are expected in or during a process section. For example it can be determined via blacklisting or whitelisting whether the process section determined was determined correctly or incorrectly. In blacklisting a blacklist comprises those data streams D1, D2 that are not provided during a process section determined. If these data streams D1, D2 are provided it is very probable that the process section determined is incorrect. In whitelisting data streams D1, D2 that can be provided during the process section determined are defined in a whitelist. If a data stream D1, D2 is provided that is not defined in this whitelist then it is very probable that the process section determined is incorrect.

The error information can in particular be provided when the process section defined is incorrect with a probability that exceeds a predefined threshold value. The threshold value can for example be 70%, 80%, 85%, 90%, 95%, 99%.

The error information can inform operating personnel about incorrect assumptions underlying the method and for this reason about errors in determination DET-1 of the current or next working step S1, . . . , S6 and thus in provision PROV-1 of the control signal of the current or next working step S1, . . . , S6 being able to occur.

As an alternative or in addition the error information can be embodied in such a way that a correction of the process section determined is initiated.

FIG. 3 shows a third exemplary embodiment of a computer-implemented method for provision PROV-3 of a control signal for carrying out a current or next working step S1, . . . , S6.

The method steps described in the description for FIG. 1 of provision PROV-1 of a plurality of data streams D1, D2, of provision PROV-2 of a list, of application APP-1 of the individual classifiers, of determination DET-1 of the current or next working step S1, . . . , S6 and of provision PROV-3 of the control signal are embodied in a similar way to the description. The method steps described in the description for FIG. 2 of determination DET-2 of the process section and of provision PROV-4 of the error information are embodied in a similar way to the description.

The method comprises a further method step of correction CORR of the process section determined as a function of the data streams D1, D2 provided.

The method step of correction CORR of the process section determined can in this case in particular be triggered or initiated by the error information. In other words the effect of the provision PROV-4 of the error information is to correct the process section determined.

For correction the data streams provided are analyzed. As described above with regard to blacklisting and whitelisting, it can be determined based on the data streams D1, D2 provided which process section has the greatest probability of being the one currently being executed. In this case a check is made as to which process section the data streams D1, D2 provided are typical of. For this it can for example be checked by which whitelist of which process section all data streams D1, D2 provided are comprised. As an alternative or in addition it can be checked by which blacklist of which process section the data streams D1, D2 provided are not comprised. The corresponding process section can then be the corrected process section.

In versions of example embodiments of the present invention, the overview data stream can additionally be taken into account in correction CORR of the process section determined. In other words the process section determined can be corrected by a combination of the data streams D1, D2 provided, including the overview data stream.

FIG. 4 shows a fourth exemplary embodiment of a computer-implemented method for provision PROV-3 of a control signal for carrying out a current or next working step S1, . . . , S6.

The method steps described in the description for FIG. 1 of provision PROV-1 of a plurality of data streams D1, D2, of provision PROV-2 of a list, of application APP-1 of the individual classifiers, of determination DET-1 of the current or next working step S1, . . . , S6 and of provision PROV-3 of the control signal are embodied in a similar way to the description. The method steps described in the description for FIG. 2 of determination DET-2 of the process section and of provision PROV-4 of the error information are embodied in a similar way to the description. The optional method step of correction CORR of the process section determined described in the description for FIG. 3 is embodied in a similar way to the description.

Each individual classifier in the fourth exemplary embodiment is assigned a confidence value K1, K2. The confidence value K1, K2 in this case specifies how suitable the corresponding individual classifier or the assigned data stream D1, D2 is for describing the current process section. In other words the confidence value K1, K2 specifies how well the current or the next working step S1, . . . , S6 can be determined with the corresponding individual classifier or as a function of the assigned data stream D1, D2. In this case it applies that the greater the assigned confidence value K1, K2 is, the better the current or next working step S1, . . . , S6 can be determined based on the corresponding individual classifier. In this case the confidence value K1, K2 can for example be greater than or equal to 0 and less than or equal to 1. The confidence value K1, K2 can be different for different individual classifiers. In particular the confidence value K1, K2 of an individual classifier can be different for different process sections. In particular this can reflect that a specific individual classifier in different process sections varies or differs in how well suited it is for describing the process.

What is more each individual classifier is assigned a threshold value Th, Th1, Th2. The function of the threshold value Th, Th1, Th2 is described below. The threshold values Th, Th1, Th2 of different individual classifiers can be different. In particular different individual classifiers can also be assigned to an individual classifier for different process sections. In other words the assigned threshold values Th, Th1, Th2 of the individual classifiers can be process section-dependent.

In the exemplary embodiment the method step of determination DET-1 of the current or next working step S1, . . . , S6 comprises a method step of determination DET-3 of the working step S1, . . . , S6 for which, with the individual classifier with the greatest confidence value K1, K2, the greatest probability p, p11, . . . , p26 was determined. The probability p, p11, . . . , p26 is compared with the threshold value Th, Th1, Th2 assigned to the individual classifier. When the probability p, p11, . . . , p26 determined is greater than the threshold value Th, Th1, Th2, the corresponding working step S1, . . . , S6 is the current or the next working step S1, . . . , S6. When the probability p, p11, . . . , p26 determined is less than or equal to the threshold value Th, Th1, Th2 of the individual classifier, the method step of determination DET-3 of the working step S1, . . . , S6 for which the greatest probability p, p11, . . . , p26 was determined, is repeated for the individual classifier to which the second greatest confidence value K1, K2 is assigned.

This method step is repeated for the individual classifiers with decreasing confidence value K1, K2 until such time as the greatest probability p, p11, . . . , p26 determined exceeds the threshold value Th, Th1, Th2 of the corresponding individual classifier. The corresponding working step S1, . . . , S6, for which the maximum probability p, p11, . . . , p26 was determined and its probability p, p11, . . . , p26 of exceeding the threshold value Th, Th1, Th2 of the individual classifier with which the probability p, p11, . . . , p26 was determined is then the current or next working step S1, . . . , S6.

A more concrete example for the method step of determination DET-1 of the current or next working step S1, . . . , S6 described in this exemplary embodiment is described in FIG. 5.

If none of the determined probabilities p, p11, . . . , p26 exceeds the corresponding assigned threshold value Th, Th1, Th2 for any of the individual classifiers, working step S1, . . . , S6 can be determined as the current or next working step S1, . . . , S6, for which with any given individual classifier the greatest probability p, p11, . . . , p26 was determined. Then, as an alternative that working step S1, . . . , S6 can be determined as the current or next working step S1, . . . , S6 for which on average over all applied individual classifiers or data streams D1, D2 the greatest probability p, p11, . . . , p26 could be determined. As an alternative that working step S1, . . . , S6 can then be determined as the current or next working step for which the greatest probability p, p11, . . . , p26 could be determined with the individual classifier with the greatest confidence value K1, K2. Then, as an alternative in such a case the method step of determination DET-1 of the current or next working step S1, . . . , S6 can be embodied as in the exemplary embodiment in accordance with the FIGS. 6 and 7.

FIG. 5 shows a first exemplary embodiment of a method step of determination DET-1 of a current or next working step S1, . . . , S6.

Described in the description for FIG. 5 is a concrete example of a method step of determination DET-1 of the current or next working step S1, . . . , S6 as described in FIG. 4.

The method step of determination DET-3 of the working step D1, . . . , S6 with the greatest probability p11, . . . , p26 is described here in detail by way of example.

The list of working steps S1, . . . , S6 provided comprises in this exemplary embodiment six working steps S1, . . . , S6. As an alternative the list can naturally comprise any other given number of working steps S1, . . . , S6. By application APP-1 of the individual classifiers to the respectively assigned data streams D1, D2 a probability p11, . . . , p26 is determined for each working step S1, . . . , S6 of the list and each data stream D1, D2. Each individual classifier and thus each data stream D1, D2 assigned to this is assigned a confidence value K1, K2 and a threshold value Th1, Th2 in each case. In this case, in the example shown, the confidence value K11 assigned to a first individual classifier or to the first data stream D1 assigned to this is greater than the confidence value K2 assigned to a second individual classifier or second data stream D2.

In the method step of determination DET-3 of the working step S1, . . . , S6 for which the greatest probability p11, . . . , p26 was determined, first of all the greatest probability of the probabilities p11, p12, p13, p14, 15, p16 determined with the first individual classifier is determined. This is shown with the dummy code max(p11, p12, p13, p14, 15, p16). In the example shown the probability p13 for the third working step S3 is determined as the maximum. This probability p13 is compared with the threshold value Th1 of the first individual classifier.

If the probability p13 is greater than the corresponding threshold value Th1, the corresponding working step S3 is the current or next working step and the corresponding control signal for carrying out this working step S3 is provided in the method step of provision PROV-3 of the control signal. In this case the method step of determination DET-1 of the current or next working step S1, . . . , S6 is completed.

If the probability p13 is less than or equal to the threshold value Th1 of the first individual classifier, the method step of determination DET-2 of the greatest probability p11, . . . , p26 is repeated for the individual classifier with the second greatest confidence value K2. In this case the working step S1, . . . , S6 is determined for which, by application APP-1 of the second individual classifier to the corresponding data stream D2, the greatest or maximum probability p26 was determined. This applies in this example to the sixth working step S6, for which the maximum probability p26 was determined. This maximum probability p26 is compared in its turn with the threshold value Th2 of the corresponding individual classifier or data stream D2 and, depending on whether the maximum probability p26 exceeds the threshold value Th2 or not, the sixth working step S6 is determined as the current or next working step or the method step is repeated once again for the individual classifier with the next smallest confidence value.

The options that pick up the case in which greatest probability does not exceed the corresponding threshold value Th1, Th2 for any of the individual classifiers D1, D2, are listed in the description for FIG. 4.

FIG. 6 shows a fifth exemplary embodiment of a computer-implemented method for provision PROV-3 of a control signal for carrying out a current or next working step S1, . . . , S6.

The method steps described in the description for FIG. 1 of provision PROV-1 of a plurality of data streams D1, D2, of provision PROV-2 of a list, of application APP-1 of the individual classifiers, of determination DET-1 of the current or next working step S1, . . . , S6 and of provision PROV-3 of the control signal are embodied in a similar way to the description. The method steps described in the description for FIG. 2 of determination DET-2 of the process section and of provision PROV-4 of the error information are embodied in a similar way to the description. The optional method step of correction CORR of the process section determined described in the description for FIG. 3 is embodied in a similar way to the description.

The exemplary embodiment described below of the method step of determination DET-1 of the current or next working step S1, . . . , S6 can be embodied as an alternative or as an expansion to the exemplary embodiment in accordance with the description for FIGS. 4 and 5.

A concrete example of the exemplary embodiment described below is given in the description for FIG. 7.

Each of the individual classifiers, as described in the description for FIG. 4, is assigned a confidence value K1, K2. The confidence value is embodied in this case as described in the description for FIG. 4 and can accordingly also be dependent on the current process section.

The method step of determination DET-1 of the current or next working step S1, . . . , S6 comprises a method step of a multiplication MULT of the probability p, p11, . . . , p26 determined for each working step S1, . . . , S6 by the confidence value K1, K2 of the individual classifier with which the respective probability p, p11, . . . , p26 was determined. In this case a weighted probability Kp11, Kp12, Kp13, Kp14, Kp15, Kp16, Kp21, Kp22, Kp23, Kp24, Kp25, Kp26 is determined for each working step S1, . . . , S6 and each data stream D1, D2 or each individual classifier.

What is more the method step of determination DET-1 of the current or next working step S1, . . . , S6 comprises a method step of addition ADD of the weighted probabilities Kp11, . . . , Kp26 of the different individual classifiers or data streams D1, D2 for each working step S1, . . . , S6. In other words, for each working step S1, . . . , S6, the weighted probabilities Kp11, . . . , Kp26 that were determined with the different individual classifiers or data streams D1, D2, are added. In this way a summed, weighted probability Kp121, Kp122, Kp123, Kp124, Kp125, Kp126 is determined for each working step S1, . . . , S6.

The working step S1, . . . , S6, for which this summed, weighted probability Kp121, . . . , Kp126 is a maximum is determined as the current or next working step S1, . . . , S6.

FIG. 7 shows a second exemplary embodiment of a method step of determination DET-1 of a current or next working step S1, . . . , S6.

Described in the description for FIG. 7 is a concrete example of a method step as described in FIG. 6 of determination DET-1 of the current or next working step S1, . . . , S6.

In particular in this case the method steps of multiplication MULT and of addition ADD are carried out for an example with a list with six working steps S1, . . . , S6 and two data streams D1, D2 and associated individual classifiers. For the sake of clarity here only two data streams D1, D2 are given. The method can naturally be carried out in a similar way with any given number of data streams D1, D2.

By application APP-1 of the respective individual classifiers to the data streams D1, D2 assigned to these, for each working step S1, . . . , S6 of the list, a probability p11, . . . , p26 is determined in each case, which specifies how probable it is that the corresponding working step S1, . . . , S6, starting from the respective data stream D1, D2, is the current or the next step carried out.

Each of these probabilities p11, . . . , p26 is multiplied in the method step of multiplication MULT by the confidence value K1, K2 of the individual classifier with which the probability p11, . . . , p26 was determined. In this case a weighted probability Kp11, . . . , Kp26 is determined for each working step S1, . . . , S6 and each data stream D1, D2 or each individual classifier.

Then, in the method step of addition ADD die weighted probabilities Kp11, . . . , Kp26 of the different data streams D1, D2 or individual classifiers are added for the same working steps S1, . . . , S6 in each case. In this case a summed, weighted probability Kp121, . . . , Kp126 is determined for each of the working steps S1, . . . , S6.

From these summed, weighted probabilities Kp121, . . . , Kp126 the maximum probability is determined. This is shown in FIG. 7 with the dummy code max(Kp121, Kp122, Kp123, Kp124, Kp125, Kp126).

The working step S1, . . . , S6, for which the summed, weighted probability Kp121, . . . , Kp126 is the maximum is then the current or next working step S1, . . . , S6 for which in the method step of provision PROV-3 of the control signal the corresponding control signal for carrying out working step S1, . . . , S6 is provided.

FIG. 8 shows a sixth exemplary embodiment of a computer-implemented method for provision PROV-3 of a control signal for carrying out a current or next working step S1, . . . , S6.

The method steps described in the description for FIG. 1 of provision PROV-1 of a plurality of data streams D1, D2, of provision PROV-2 of a list, of application APP-1 of the individual classifiers, of determination DET-1 of the current or next working step S1, . . . , S6 and of provision PROV-3 of the control signal are embodied in a similar way to the description. The method steps described in the description for FIG. 2 of determination DET-2 of the process section and of provision PROV-4 of the error information are embodied in a similar way to the description. The optional method step of correction CORR of the process section determined described in the description for FIG. 3 is embodied in a similar way to the description.

The exemplary embodiment describes a further alternate or additional version of the method step of determination DET-1 of the current or next working step S1, . . . , S6. In accordance with the exemplary embodiment the method step of determination DET-1 of the current or next working step S1, . . . , S6 comprises a method step of application APP-2 of a trained function to the probabilities p, p11, p12, . . . , p26 determined for each working step S1, . . . , S6 and each individual classifier or data stream D1, D2. In this case the current or next working step S1, . . . , S6 is determined.

In versions of example embodiments of the present invention, on application App-2 of the trained function the confidence value K1, K2 of the individual classifier with which the corresponding probability p, p11, . . . , p26 was determined can also be taken into account for each of the probabilities p, p11, . . . , p26.

FIG. 9 shows a seventh exemplary embodiment of a computer-implemented method for provision PROV-3 of a control signal for carrying out a current or next working step S1, . . . , S6.

The method steps described in the description for FIG. 1 of provision PROV-1 of a plurality of data streams D1, D2, of provision PROV-2 of a list, of application APP-1 of the individual classifiers, of determination DET-1 of the current or next working step S1, . . . , S6 and of provision PROV-3 of the control signal are embodied in a similar way to the description. The method steps described in the description for FIG. 2 of determination DET-2 of the process section and of provision PROV-4 of the error information are embodied in a similar way to the description. The optional method step of correction CORR of the process section determined described in the description for FIG. 3 is embodied in a similar way to the description.

The method step of determination DET-1 of the current or next working step S1, . . . , S6 can in particular also be embodied in accordance with an exemplary embodiment or a combination of the exemplary embodiments in accordance with the descriptions for FIGS. 4 to 8.

What is more the method comprises a method step of determination DET-4 of a selection of individual classifiers. In this case the selection can depend on the current process section. In this case, in the method step of application APP-1 of the individual classifiers, only the selected individual classifiers are applied in each case to the correspondingly assigned data streams D1, D2 provided.

The selection can be based in versions of example embodiments of the present invention, on the confidence values K1, K2 of the individual classifiers embodied with regard to FIG. 4. In this case only those individual classifiers are selected for which the confidence value K1, K2 exceeds a predefined threshold value.

As an alternative the selection of individual classifiers can be based on only the individual classifiers being taken into account about which it is known that the associated data streams D1, D2 give a good description of the process in the current process section. In this case "good" means that it is known from experience that the corresponding data streams D1, D2 are suitable for determining the current or next working step S1, . . . , S6.

FIG. 10 shows an exemplary embodiment of a computer-implemented method for provision of an individual classifier.

The method describes a training of an individual classifier that can be applied or used in one of the exemplary embodiments described in the FIGS. 1 to 9.

In a method step of provision TPROV-1 of a training data stream, the training data stream is received in particular for training of the individual classifier. In this case the training data is embodied in such a way that the individual classifier is embodied to be applied to the training data stream. In particular the training data stream can be provided with a system that is also embodied to provide the data stream D1, D2 in one of the methods described above. In other words the training data stream is embodied similarly to the data stream D1, D2 that is to be applied later to the individual classifier.

In a method step of provision TPOV-2 of a list, a list is received that comprises a plurality of working steps. The list is embodied in this case as a described with regard to FIG. 1. In addition to the characteristics of the list described in FIG. 1, each of the working steps of the list is assigned a training probability, which is embodied like the probabilities described with regard to FIG. 1.

The training probability can have been determined manually.

In this case the training data stream can originate from an already completed process. The training data stream can abort at any given point in time of the process for which the current or next working step is to be determined. Since the process is already completed however, it is also known what the current or next working step is. This knowledge can be used to determine the training probabilities. In particular the training probabilities can be determined manually based on this knowledge.

As an alternative the training probability, as described with regard to FIG. 1, can correspond to a probability that has been determined with another individual classifier for the same working steps. In this case the probability was determined with the other individual classifier by application to a data stream that was acquired or provided in parallel to or simultaneously with the training data stream. The probabilities determined with the other individual classifier are also referred to as the classification result.

In a method step of training TRAIN the individual classifier is applied to the training data stream. In this case a probability is determined for each working step of the list. This probability determined is then compared for each working step with the training probability of the corresponding working step. The individual classifier is adapted in such a way that, when the individual classifier is applied once again to the training data stream, the probabilities determined and the training probabilities are a better match.

The method step of training TRAIN can be repeated for a plurality of suitable training data streams. As an alternative or in addition the training data stream can be aborted or interrupted at different points in time. The individual classifier can then however be trained for the same training data stream for different points in time with the method described above.

In particular the method step of training TRAIN can be repeated until such time as an abort criterion is fulfilled. The abort criterion can specify in this case how often the method step of training TRAIN is to be carried out at a maximum. As an alternative or in addition the abort criterion can specify how sharply probabilities determined and the training probabilities are permitted to deviate from one another at a maximum or how great the deviation is permitted to be at a maximum. When the deviation is smaller than the maximum deviation the training method can be aborted.

FIG. 11 shows a provision system SYS for provision of a control signal for application APP-1 of a current or next working step S1, . . . , S6. FIG. 12 shows a training system TSYS for provision of an individual classifier.

The provision system SYS shown for provision of a control signal for carrying out a current or next working step is embodied for carrying out an inventive method for provision of a control signal for carrying out a current or next working step. The provision system SYS comprises an interface SYS.IF, a computing unit SYS.CU and a memory unit SYS.MU. The training system TSYS shown for provision of an individual classifier is embodied for carrying out an inventive method for provision of an individual classifier. The training system TSYS comprises a training interface TSYS.IF, a training computing unit TSYS.CU and a training memory unit TSYS.MU.

The provision system SYS and/or the training system TSYS can in particular be a computer, a microcontroller or an integrated circuit (IC). As an alternative the provision system SYS and/or the training system TSYS can be a real or virtual computer network (a technical term for a real computer network is cluster, a technical term for a virtual computer network is Cloud). The provision system SYS and/or the training system TSYS can be embodied as a virtual system that is executed on a computer or a real computer network or a virtual computer network (a technical term is virtualization).

The interface SYS.IF and/or the training interface TSYS.IF can be a hardware or software interface (for example a PCI bus, USB or Firewire). The computing unit SYS.CU and/or the training computing unit TSYS.CU can comprise hardware and/or software components, for example a microprocessor or what is known as an FPGA (Field Programmable Gate Array). The memory unit SYS.MU and/or the training memory unit TSYS.MU can be embodied as permanent working memory (Random Access Memory, RAM) as permanent mass storage (hard disk, USB stick, SD card, Solid State Disk (SSD)).

The interface SYS.IF and/or the training interface TSYS.IF can in particular comprise a plurality of sub-interfaces, which carry out different method steps of the respective inventive method. In other words the interface SYS.IF and/or the training interface TSYS.IF can be embodied as a plurality of interfaces SYS.IF and/or training interfaces TSYS.IF. The computing unit SYS.CU and/or the training computing unit TSYS.CU can in particular comprise a plurality of sub-computing units, which carry out different method steps of the respective inventive method. In other words the computing unit SYS.CU and/or the training computing unit TSYS.CU can be embodied as a plurality of computing units SYS.CU and/or training computing units TSYS.CU.

It will be understood that, although the terms first, second, etc. may be used herein to describe various elements, components, regions, layers, and/or sections, these elements, components, regions, layers, and/or sections, should not be limited by these terms. These terms are only used to distinguish one element from another. For example, a first element could be termed a second element, and, similarly, a second element could be termed a first element, without departing from the scope of example embodiments. As used herein, the term "and/or," includes any and all combinations of one or more of the associated listed items. The phrase "at least one of" has the same meaning as "and/or".

Spatially relative terms, such as "beneath," "below," "lower," "under," "above," "upper," and the like, may be used herein for ease of description to describe one element or feature's relationship to another element(s) or feature(s) as illustrated in the figures. It will be understood that the spatially relative terms are intended to encompass different orientations of the device in use or operation in addition to the orientation depicted in the figures. For example, if the device in the figures is turned over, elements described as "below," "beneath," or "under," other elements or features would then be oriented "above" the other elements or features. Thus, the example terms "below" and "under" may encompass both an orientation of above and below. The device may be otherwise oriented (rotated 90 degrees or at other orientations) and the spatially relative descriptors used herein interpreted accordingly. In addition, when an element is referred to as being "between" two elements, the element may be the only element between the two elements, or one or more other intervening elements may be present.

Spatial and functional relationships between elements (for example, between modules) are described using various terms, including "on," "connected," "engaged," "interfaced," and "coupled." Unless explicitly described as being "direct," when a relationship between first and second elements is described in the disclosure, that relationship encompasses a direct relationship where no other intervening elements are present between the first and second elements, and also an indirect relationship where one or more intervening elements are present (either spatially or functionally) between the first and second elements. In contrast, when an element is referred to as being "directly" on, connected, engaged, interfaced, or coupled to another element, there are no intervening elements present. Other words used to describe the relationship between elements should be interpreted in a like fashion (e.g., "between," versus "directly between," "adjacent," versus "directly adjacent," etc.).

The terminology used herein is for the purpose of describing particular embodiments only and is not intended to be limiting of example embodiments. As used herein, the singular forms "a," "an," and "the," are intended to include the plural forms as well, unless the context clearly indicates otherwise. As used herein, the terms "and/or" and "at least one of" include any and all combinations of one or more of the associated listed items. It will be further understood that the terms "comprises," "comprising," "includes," and/or "including," when used herein, specify the presence of stated features, integers, steps, operations, elements, and/or components, but do not preclude the presence or addition of one or more other features, integers, steps, operations, elements, components, and/or groups thereof. As used herein, the term "and/or" includes any and all combinations of one or more of the associated listed items. Expressions such as "at least one of," when preceding a list of elements, modify the entire list of elements and do not modify the individual elements of the list. Also, the term "example" is intended to refer to an example or illustration.

It should also be noted that in some alternative implementations, the functions/acts noted may occur out of the order noted in the figures. For example, two figures shown in succession may in fact be executed substantially concurrently or may sometimes be executed in the reverse order, depending upon the functionality/acts involved.

Unless otherwise defined, all terms (including technical and scientific terms) used herein have the same meaning as commonly understood by one of ordinary skill in the art to which example embodiments belong. It will be further understood that terms, e.g., those defined in commonly used dictionaries, should be interpreted as having a meaning that is consistent with their meaning in the context of the relevant art and will not be interpreted in an idealized or overly formal sense unless expressly so defined herein.

It is noted that some example embodiments may be described with reference to acts and symbolic representations of operations (e.g., in the form of flow charts, flow diagrams, data flow diagrams, structure diagrams, block diagrams, etc.) that may be implemented in conjunction with units and/or devices discussed above. Although discussed in a particularly manner, a function or operation specified in a specific block may be performed differently from the flow specified in a flowchart, flow diagram, etc. For example, functions or operations illustrated as being performed serially in two consecutive blocks may actually be performed simultaneously, or in some cases be performed in reverse order. Although the flowcharts describe the operations as sequential processes, many of the operations may be performed in parallel, concurrently or simultaneously. In addition, the order of operations may be re-arranged. The processes may be terminated when their operations are completed, but may also have additional steps not included in the figure. The processes may correspond to methods, functions, procedures, subroutines, subprograms, etc.

Specific structural and functional details disclosed herein are merely representative for purposes of describing example embodiments. The present invention may, however, be embodied in many alternate forms and should not be construed as limited to only the embodiments set forth herein.

In addition, or alternative, to that discussed above, units and/or devices according to one or more example embodiments may be implemented using hardware, software, and/or a combination thereof. For example, hardware devices may be implemented using processing circuitry such as, but not limited to, a processor, Central Processing Unit (CPU), a controller, an arithmetic logic unit (ALU), a digital signal processor, a microcomputer, a field programmable gate array (FPGA), a System-on-Chip (SoC), a programmable logic unit, a microprocessor, or any other device capable of responding to and executing instructions in a defined manner. Portions of the example embodiments and corresponding detailed description may be presented in terms of software, or algorithms and symbolic representations of operation on data bits within a computer memory. These descriptions and representations are the ones by which those of ordinary skill in the art effectively convey the substance of their work to others of ordinary skill in the art. An algorithm, as the term is used here, and as it is used generally, is conceived to be a self-consistent sequence of steps leading to a desired result. The steps are those requiring physical manipulations of physical quantities. Usually, though not necessarily, these quantities take the form of optical, electrical, or magnetic signals capable of being stored, transferred, combined, compared, and otherwise manipulated. It has proven convenient at times, principally for reasons of common usage, to refer to these signals as bits, values, elements, symbols, characters, terms, numbers, or the like.

It should be borne in mind that all of these and similar terms are to be associated with the appropriate physical quantities and are merely convenient labels applied to these quantities. Unless specifically stated otherwise, or as is apparent from the discussion, terms such as "processing" or "computing" or "calculating" or "determining" of "displaying" or the like, refer to the action and processes of a computer system, or similar electronic computing device/hardware, that manipulates and transforms data represented as physical, electronic quantities within the computer system's registers and memories into other data similarly represented as physical quantities within the computer system memories or registers or other such information storage, transmission or display devices.

In this application, including the definitions below, the term 'module' or the term 'controller' may be replaced with the term 'circuit.' The term 'module' may refer to, be part of, or include processor hardware (shared, dedicated, or group) that executes code and memory hardware (shared, dedicated, or group) that stores code executed by the processor hardware.

The module may include one or more interface circuits. In some examples, the interface circuits may include wired or wireless interfaces that are connected to a local area network (LAN), the Internet, a wide area network (WAN), or combinations thereof. The functionality of any given module of the present disclosure may be distributed among multiple modules that are connected via interface circuits. For example, multiple modules may allow load balancing. In a further example, a server (also known as remote, or cloud) module may accomplish some functionality on behalf of a client module.

Software may include a computer program, program code, instructions, or some combination thereof, for independently or collectively instructing or configuring a hardware device to operate as desired. The computer program and/or program code may include program or computer-readable instructions, software components, software modules, data files, data structures, and/or the like, capable of being implemented by one or more hardware devices, such as one or more of the hardware devices mentioned above. Examples of program code include both machine code produced by a compiler and higher level program code that is executed using an interpreter.

For example, when a hardware device is a computer processing device (e.g., a processor, Central Processing Unit (CPU), a controller, an arithmetic logic unit (ALU), a digital signal processor, a microcomputer, a microprocessor, etc.), the computer processing device may be configured to carry out program code by performing arithmetical, logical, and input/output operations, according to the program code. Once the program code is loaded into a computer processing device, the computer processing device may be programmed to perform the program code, thereby transforming the computer processing device into a special purpose computer processing device. In a more specific example, when the program code is loaded into a processor, the processor becomes programmed to perform the program code and operations corresponding thereto, thereby transforming the processor into a special purpose processor.

Software and/or data may be embodied permanently or temporarily in any type of machine, component, physical or virtual equipment, or computer storage medium or device, capable of providing instructions or data to, or being interpreted by, a hardware device. The software also may be distributed over network coupled computer systems so that the software is stored and executed in a distributed fashion. In particular, for example, software and data may be stored by one or more computer readable recording mediums, including the tangible or non-transitory computer-readable storage media discussed herein.

Even further, any of the disclosed methods may be embodied in the form of a program or software. The program or software may be stored on a non-transitory computer readable medium and is adapted to perform any one of the aforementioned methods when run on a computer device (a device including a processor). Thus, the non-transitory, tangible computer readable medium, is adapted to store information and is adapted to interact with a data processing facility or computer device to execute the program of any of the above mentioned embodiments and/or to perform the method of any of the above mentioned embodiments.

Example embodiments may be described with reference to acts and symbolic representations of operations (e.g., in the form of flow charts, flow diagrams, data flow diagrams, structure diagrams, block diagrams, etc.) that may be implemented in conjunction with units and/or devices discussed in more detail below. Although discussed in a particularly manner, a function or operation specified in a specific block may be performed differently from the flow specified in a flowchart, flow diagram, etc. For example, functions or operations illustrated as being performed serially in two consecutive blocks may actually be performed simultaneously, or in some cases be performed in reverse order.

According to one or more example embodiments, computer processing devices may be described as including various functional units that perform various operations and/or functions to increase the clarity of the description. However, computer processing devices are not intended to be limited to these functional units. For example, in one or more example embodiments, the various operations and/or functions of the functional units may be performed by other ones of the functional units. Further, the computer processing devices may perform the operations and/or functions of the various functional units without sub-dividing the operations and/or functions of the computer processing units into these various functional units.

Units and/or devices according to one or more example embodiments may also include one or more storage devices. The one or more storage devices may be tangible or non-transitory computer-readable storage media, such as random access memory (RAM), read only memory (ROM), a permanent mass storage device (such as a disk drive), solid state (e.g., NAND flash) device, and/or any other like data storage mechanism capable of storing and recording data. The one or more storage devices may be configured to store computer programs, program code, instructions, or some combination thereof, for one or more operating systems and/or for implementing the example embodiments described herein. The computer programs, program code, instructions, or some combination thereof, may also be loaded from a separate computer readable storage medium into the one or more storage devices and/or one or more computer processing devices using a drive mechanism. Such separate computer readable storage medium may include a Universal Serial Bus (USB) flash drive, a memory stick, a Blu-ray/DVD/CD-ROM drive, a memory card, and/or other like computer readable storage media. The computer programs, program code, instructions, or some combination thereof, may be loaded into the one or more storage devices and/or the one or more computer processing devices from a remote data storage device via a network interface, rather than via a local computer readable storage medium. Additionally, the computer programs, program code, instructions, or some combination thereof, may be loaded into the one or more storage devices and/or the one or more processors from a remote computing system that is configured to transfer and/or distribute the computer programs, program code, instructions, or some combination thereof, over a network. The remote computing system may transfer and/or distribute the computer programs, program code, instructions, or some combination thereof, via a wired interface, an air interface, and/or any other like medium.

The one or more hardware devices, the one or more storage devices, and/or the computer programs, program code, instructions, or some combination thereof, may be specially designed and constructed for the purposes of the example embodiments, or they may be known devices that are altered and/or modified for the purposes of example embodiments.

A hardware device, such as a computer processing device, may run an operating system (OS) and one or more software applications that run on the OS. The computer processing device also may access, store, manipulate, process, and create data in response to execution of the software. For simplicity, one or more example embodiments may be exemplified as a computer processing device or processor; however, one skilled in the art will appreciate that a hardware device may include multiple processing elements or processors and multiple types of processing elements or processors. For example, a hardware device may include multiple processors or a processor and a controller. In addition, other processing configurations are possible, such as parallel processors.

The computer programs include processor-executable instructions that are stored on at least one non-transitory computer-readable medium (memory). The computer programs may also include or rely on stored data. The computer programs may encompass a basic input/output system (BIOS) that interacts with hardware of the special purpose computer, device drivers that interact with particular devices of the special purpose computer, one or more operating systems, user applications, background services, background applications, etc. As such, the one or more processors may be configured to execute the processor executable instructions.

The computer programs may include: (i) descriptive text to be parsed, such as HTML (hypertext markup language) or XML (extensible markup language), (ii) assembly code, (iii) object code generated from source code by a compiler, (iv) source code for execution by an interpreter, (v) source code for compilation and execution by a just-in-time compiler, etc. As examples only, source code may be written using syntax from languages including C, C++, C#, Objective-C, Haskell, Go, SQL, R, Lisp, Java®, Fortran, Perl, Pascal, Curl, OCaml, Javascript®, HTML5, Ada, ASP (active server pages), PHP, Scala, Eiffel, Smalltalk, Erlang, Ruby, Flash®, Visual Basic®, Lua, and Python®.

Further, at least one example embodiment relates to the non-transitory computer-readable storage medium including electronically readable control information (processor executable instructions) stored thereon, configured in such that when the storage medium is used in a controller of a device, at least one embodiment of the method may be carried out.

The computer readable medium or storage medium may be a built-in medium installed inside a computer device main body or a removable medium arranged so that it can be separated from the computer device main body. The term computer-readable medium, as used herein, does not encompass transitory electrical or electromagnetic signals propagating through a medium (such as on a carrier wave); the term computer-readable medium is therefore considered tangible and non-transitory. Non-limiting examples of the non-transitory computer-readable medium include, but are not limited to, rewriteable non-volatile memory devices (including, for example flash memory devices, erasable programmable read-only memory devices, or a mask read-only memory devices); volatile memory devices (including, for example static random access memory devices or a dynamic random access memory devices); magnetic storage media (including, for example an analog or digital magnetic tape or a hard disk drive); and optical storage media (including, for example a CD, a DVD, or a Blu-ray Disc). Examples of the media with a built-in rewriteable non-volatile memory, include but are not limited to memory cards; and media with a built-in ROM, including but not limited to ROM cassettes; etc. Furthermore, various information regarding stored images, for example, property information, may be stored in any other form, or it may be provided in other ways.

The term code, as used above, may include software, firmware, and/or microcode, and may refer to programs, routines, functions, classes, data structures, and/or objects. Shared processor hardware encompasses a single microprocessor that executes some or all code from multiple modules. Group processor hardware encompasses a microprocessor that, in combination with additional microprocessors, executes some or all code from one or more modules. References to multiple microprocessors encompass multiple microprocessors on discrete dies, multiple microprocessors on a single die, multiple cores of a single microprocessor, multiple threads of a single microprocessor, or a combination of the above.

Shared memory hardware encompasses a single memory device that stores some or all code from multiple modules. Group memory hardware encompasses a memory device that, in combination with other memory devices, stores some or all code from one or more modules.

The term memory hardware is a subset of the term computer-readable medium. The term computer-readable medium, as used herein, does not encompass transitory electrical or electromagnetic signals propagating through a medium (such as on a carrier wave); the term computer-readable medium is therefore considered tangible and non-transitory. Non-limiting examples of the non-transitory computer-readable medium include, but are not limited to, rewriteable non-volatile memory devices (including, for example flash memory devices, erasable programmable read-only memory devices, or a mask read-only memory devices); volatile memory devices (including, for example static random access memory devices or a dynamic random access memory devices); magnetic storage media (including, for example an analog or digital magnetic tape or a hard disk drive); and optical storage media (including, for example a CD, a DVD, or a Blu-ray Disc). Examples of the media with a built-in rewriteable non-volatile memory, include but are not limited to memory cards; and media with a built-in ROM, including but not limited to ROM cassettes; etc. Furthermore, various information regarding stored images, for example, property information, may be stored in any other form, or it may be provided in other ways.

The apparatuses and methods described in this application may be partially or fully implemented by a special purpose computer created by configuring a general purpose computer to execute one or more particular functions embodied in computer programs. The functional blocks and flowchart elements described above serve as software specifications, which can be translated into the computer programs by the routine work of a skilled technician or programmer.

Although described with reference to specific examples and drawings, modifications, additions and substitutions of example embodiments may be variously made according to the description by those of ordinary skill in the art. For example, the described techniques may be performed in an order different with that of the methods described, and/or components such as the described system, architecture, devices, circuit, and the like, may be connected or combined to be different from the above-described methods, or results may be appropriately achieved by other components or equivalents.

Although the present invention has been shown and described with respect to certain example embodiments, equivalents and modifications will occur to others skilled in the art upon the reading and understanding of the specification. The present invention includes all such equivalents and modifications and is limited only by the scope of the appended claims.

Where this has not occurred explicitly but is meaningful in the sense of the present invention, individual exemplary embodiments, individual subaspects or features thereof can be combined with one another or exchanged for one another without departing from the framework of the current invention. Advantages of the present invention described with regard to one exemplary embodiment also apply, without this being explicitly stated, where transferrable, to other exemplary embodiments.

What is claimed is:

1. A computer-implemented method for provision of a control signal for carrying out a current or next working step in a process, the computer-implemented method comprising:
provisioning a plurality of data streams, wherein
the process is divided into a plurality of consecutive process sections,
the plurality of data streams depend on a process section of the process, and
each of the plurality of data streams is uniquely assigned an individual classifier from among a plurality of individual classifiers;
provisioning a list including a plurality of possible working steps;
applying the plurality of individual classifiers to the plurality of data streams, wherein
each individual classifier, based on the data stream assigned for each corresponding working step, determines a probability that the corresponding working step is being carried out as the current or next working step;
determining the current or next working step as a function of the determined probabilities; and
provisioning the control signal for carrying out the current or next working step.

2. The computer-implemented method as claimed in claim 1, wherein
a data stream among the plurality of data streams is provided is an overview data stream,
the overview data stream is provided during the process,
the overview data stream is provided by a camera filming the process or via fluoroscopy, and
the computer-implemented method includes determining the process section as a function of the overview data stream.

3. The computer-implemented method as claimed in claim 2, wherein
data streams provided in a process section are known, and
the computer-implemented method includes provisioning error information, which specifies that the process section determined is incorrect when an unexpected data stream is provided in the process section determined.

4. The computer-implemented method as claimed in claim 3, further comprising:
correcting the process section determined as a function of the plurality of data streams.

5. The computer-implemented method as claimed in claim 2, wherein the plurality of individual classifiers are trained individually at least one of centrally or in an institution in which the process is carried out, and wherein locations of the training of the plurality of individual classifiers are different for different ones of the plurality of individual classifiers.

6. The computer-implemented method as claimed in claim 2, wherein the control signal is configured to control at least one of a medical system or an indication for operating personnel.

7. The computer-implemented method as claimed in claim 2, wherein
each of the plurality of individual classifiers is assigned a confidence value and a threshold value,
the determining of the current or next working step includes determining a working step for which, with a corresponding individual classifier with a greatest confidence value, a greatest probability has been determined,
in response to the greatest probability being greater than the threshold value for the corresponding individual classifier, the working step is the current or next working step, and
in response to the greatest probability being less than or equal to the threshold value of the corresponding individual classifier, the determining of the current or next working step is repeated iteratively for an individual classifier with a next smallest confidence value until such time as a probability of the working step is determined to exceed the threshold value assigned to the corresponding individual classifier.

8. The computer-implemented method as claimed in claim 2, wherein
each of the plurality of individual classifiers is assigned a confidence value,
the determining of the current or next working step includes
multiplying the probability determined for each working step by the confidence value assigned to a corresponding individual classifier, wherein
for each working step, a weighted probability is determined as a function of the corresponding individual classifier,
adding the weighted probabilities of different ones of individual classifiers for each working step, wherein
for each working step, a summed weighted probability is determined, and
the working step, for which the summed weighted probability is the greatest, is determined as the current or next working step.

9. The computer-implemented method as claimed in claim 1, wherein the plurality of data streams are carried out as a function of an institution in which the process is carried out.

10. The computer-implemented method as claimed in claim 9, wherein
in each process section, an individual classifier among the plurality of individual classifiers is a base classifier,
a data stream to which the base classifier is assigned is provided in each institution in at least a process section in which the base classifier is provided, and
other data streams of the plurality of data streams expected in the process are provided depending on the institution.

11. The computer-implemented method as claimed in claim 1, wherein the plurality of individual classifiers are trained individually at least one of centrally or in an institution in which the process is carried out, and wherein locations of the training of the plurality of individual classifiers are different for different ones of the plurality of individual classifiers.

12. The computer-implemented method as claimed in claim 11, wherein at least one of the plurality of individual classifiers is pre-trained centrally and is continuously retrained in the institution.

13. The computer-implemented method as claimed in claim 11, wherein a classification result provided by one of the plurality of individual classifiers is used for supervised training of another of the plurality of individual classifiers in the institution.

14. The computer-implemented method as claimed in claim 1, wherein the control signal is configured to control at least one of a medical system or an indication for operating personnel.

15. The computer-implemented method as claimed in claim 1, wherein the control signal comprises information about a length of the current or next working step.

16. The computer-implemented method as claimed in claim 1, wherein
each of the plurality of individual classifiers is assigned a confidence value and a threshold value,
the determining of the current or next working step includes determining a working step for which, with a corresponding individual classifier with a greatest confidence value, a greatest probability has been determined,
in response to the greatest probability being greater than the threshold value for the corresponding individual classifier, the working step is the current or next working step, and
in response to the greatest probability being less than or equal to the threshold value of the corresponding individual classifier, the determining of the current or next working step is repeated iteratively for an individual classifier with a next smallest confidence value until such time as a probability of the working step is determined to exceed the threshold value assigned to the corresponding individual classifier.

17. The computer-implemented method as claimed in claim 16, wherein the threshold value for each individual classifier depends on the process section.

18. The computer-implemented method as claimed in claim 16, wherein the confidence values assigned to the plurality of individual classifiers depend on the process section.

19. The computer-implemented method as claimed in claim 1, wherein
each of the plurality of individual classifiers is assigned a confidence value,
the determining of the current or next working step includes
multiplying the probability determined for each working step by the confidence value assigned to a corresponding individual classifier, wherein
for each working step, a weighted probability is determined as a function of the corresponding individual classifier,
adding the weighted probabilities of different ones of individual classifiers for each working step, wherein for each working step, a summed weighted probability is determined, and
the working step, for which the summed weighted probability is the greatest, is determined as the current or next working step.

20. The computer-implemented method as claimed in claim 1, wherein the determining of the current or next working step comprises:
applying a trained function to the probability determined for each working step and each individual classifier, to determine the current or next working step.

21. The computer-implemented method as claimed in claim 1, further comprising:
determining a selection of individual classifiers from the plurality of individual classifiers for the process section as a function of the plurality of data streams, and wherein in applying the plurality of individual classifiers, the selection of individual classifiers is applied to a corresponding selection of data streams.

22. The computer-implemented method as claimed in claim 1, wherein the plurality of data streams include fluoroscopy recordings, film recordings, ECG recordings, sound recordings, a user input, or system information.

23. A non-transitory computer program product including a computer program, which is loadable into a memory of a provision system, the computer program including program sections for carrying out the computer-implemented method as claimed in claim 1 when the program sections are executed by the provision system.

24. A non-transitory computer-readable storage medium on which program sections are stored, the program sections, when executed at a provision system, cause the provision system to perform the computer-implemented method as claimed in claim 1.

25. A provision system for provision of a control signal for carrying out a current or next working step in a process, the provision system comprising:
an interface configured to
provision a plurality of data streams,
provision a list including a plurality of possible working steps, and
provision a control signal for carrying out the current or next working step, wherein
the plurality of data streams depend on a process section of the process,
each of the plurality of data streams is uniquely assigned an individual classifier from among
a plurality of individual classifiers; and
at least one processor configured to
apply the plurality of individual classifiers to the plurality of data streams, wherein
each individual classifier, based on the data stream assigned, determines a probability for each corresponding working step, the probability specifying a probability that the corresponding working step is the current or next step, and determine the current or next working step as a
function of the determined probabilities.

* * * * *